United States Patent
Kawahara et al.

(10) Patent No.: US 10,508,292 B2
(45) Date of Patent: *Dec. 17, 2019

(54) METHOD OF PRODUCING LIPID

(71) Applicant: Kao Corporation, Chuo-ku, Tokyo (JP)

(72) Inventors: Akihito Kawahara, Wakayama (JP); Shinji Sugihara, Wakayama (JP)

(73) Assignee: Kao Corporation, Tokyo (JP)

( * ) Notice: Subject to any disclaimer, the term of this patent is extended or adjusted under 35 U.S.C. 154(b) by 54 days.

This patent is subject to a terminal disclaimer.

(21) Appl. No.: 15/572,631

(22) PCT Filed: May 20, 2016

(86) PCT No.: PCT/JP2016/065005
§ 371 (c)(1),
(2) Date: Nov. 8, 2017

(87) PCT Pub. No.: WO2016/190238
PCT Pub. Date: Dec. 1, 2016

(65) Prior Publication Data
US 2018/0135084 A1 May 17, 2018

(30) Foreign Application Priority Data

May 22, 2015 (JP) .................. 2015-104991

(51) Int. Cl.
*C12P 7/64* (2006.01)
*C12N 15/74* (2006.01)
*C12N 9/10* (2006.01)
*C12N 9/16* (2006.01)
*C12N 15/52* (2006.01)

(52) U.S. Cl.
CPC .................. *C12P 7/64* (2013.01); *C12N 9/10* (2013.01); *C12N 9/1029* (2013.01); *C12N 9/16* (2013.01); *C12N 15/52* (2013.01); *C12P 7/6409* (2013.01); *C12Y 203/01041* (2013.01)

(58) Field of Classification Search
None
See application file for complete search history.

(56) References Cited

U.S. PATENT DOCUMENTS

| | | | |
|---|---|---|---|
| 9,828,613 | B2 | 11/2017 | Ozaki |
| 10,066,248 | B2 | 9/2018 | Sugihara et al. |
| 10,337,037 | B2 | 7/2019 | Ozaki et al. |
| 2009/0298143 | A1* | 12/2009 | Roessler ............... C12N 9/16 435/134 |
| 2013/0316410 | A1 | 11/2013 | Franklin et al. |
| 2015/0307860 | A1 | 10/2015 | Ozaki et al. |
| 2016/0130615 | A1 | 5/2016 | Ozaki |
| 2017/0044580 | A1 | 2/2017 | Sugihara et al. |
| 2017/0107545 | A1 | 4/2017 | Tojo et al. |
| 2017/0114376 | A1 | 4/2017 | Ozaki et al. |
| 2017/0335353 | A1 | 11/2017 | Ozaki |
| 2017/0335354 | A1 | 11/2017 | Ozaki |

FOREIGN PATENT DOCUMENTS

| | | |
|---|---|---|
| JP | 2011-505838 A | 3/2011 |
| WO | WO 98/46776 A2 | 10/1998 |
| WO | WO 2009/076559 A1 | 6/2009 |
| WO | WO 2014/103930 A1 | 7/2014 |
| WO | WO 2015/005139 A1 | 1/2015 |
| WO | WO 2015/133305 A1 | 9/2015 |
| WO | WO 2015/194628 A1 | 12/2015 |
| WO | WO 2016/021481 A1 | 2/2016 |
| WO | WO 2016/076231 A1 | 5/2016 |
| WO | WO 2016/088511 A1 | 6/2016 |
| WO | WO 2017/022740 A1 | 2/2017 |

OTHER PUBLICATIONS

Zhou et al., Cell Mol Life Sci 63:2260-2290, 2006 (Year: 2006).*
Kozak, M., Gene 234:187-208, 1999 (Year: 1999).*
Excerpted file history, U.S. Appl. No. 15/110,635: Notice of Allowance and Fees Due (dated May 9, 2018); Terminal Disclaimer review decision (Apr. 5, 2018); Amendment and reply after non-final rejection (dated Apr. 4, 2018); Terminal Disclaimer filed (Apr. 4, 2018); Non-Final Rejection (dated Jan. 11, 2018); Response to restriction/election of species (Dec. 11, 2017); preliminary amendment (dated Dec. 11, 2017); Restriction/election of species (Oct. 12, 2017); Preliminary amendment (dated Sep. 26, 2018); preliminary amendment (dated Jul. 8, 2016).
International Search Report (ISR) for PCT/JP2016/065005; I.A. fd May 20, 2016, dated Aug. 16, 2016 from the Japan Patent Office, Tokyo, Japan.
International Preliminary Report on Patentability (IPRP), Chapter 1 of the Patent Cooperation Treaty, including the Written Opinion for PCT/JP2016/065005; I.A. fd May 20, 2016, dated Nov. 28, 2017, by the International Bureau of WIPO, Geneva, Switzerland.
Genbank[online], Accession No. EWM28742, Corteggiani, CE et al., "3-oxoacyl-(acyl-carrier-protein) synthase 2 [Nannochloropsis gaditana]," PCT/JP2016/065005; I.A. fd May 20, 2016 <url: http://www.ncbi.nlm.nih.gov/protein/EWM28742. 1>Feb. 14, 2014.
Dehesh, K. et al., "KAS IV: a 3-ketoacyl-ACP synthase from *Cuphea* sp. is a medium chain specific condensing enzyme," Plant J. Aug. 1998;15(3):383-90. Blackwell Science Ltd., Oxford, England.

(Continued)

*Primary Examiner* — David Steadman

(74) *Attorney, Agent, or Firm* — Sterne, Kessler, Goldstein & Fox P.L.L.C.

(57) ABSTRACT

A method of producing a lipid, containing the steps of culturing a transformant obtained by introducing a gene encoding the following protein (a) or (b) into cyanobacteria, and producing a lipid: (a) a protein consisting of the amino acid sequence set forth in SEQ ID NO: 1; and (b) a protein consisting of an amino acid sequence having 60% or more identity with the amino acid sequence of the protein (a), and having β-ketoacyl-ACP synthase activity.

19 Claims, No Drawings
Specification includes a Sequence Listing.

(56) References Cited

OTHER PUBLICATIONS

Liu, X et al., "Fatty acid production in genetically modified cyanobacteria," Proc Natl Acad Sci U S A. Apr. 26, 2011;108(17):6899-904. doi: 10.1073/pnas.1103014108. Epub Apr. 11, 2011, National Academy of Sciences, Washington, DC.
Gouveia, L et al., "Microalgae as a raw material for biofuels production," J Ind Microbiol Biotechnol. Feb. 2009;36(2):269-74. doi: 10.1007/s10295-008-0495-6. Epub Nov. 4, 2008.
Excerpted file history, U.S. Appl. No. 15/747,936, issue notification (Jun. 12, 2019); Notice of Allowance and Fee(s) Due including the Notice of Allowability (dated Apr. 19, 2019), Examiner-Initiated Interview Summary (dated Apr. 19, 2019); and Preliminary Amendment (dated Jan. 26, 2018), downloaded Jul. 24, 2019 from the United States Patent and Trademark Office, Alexandria, VA.

\* cited by examiner

SEQUENCE LISTING

```
<160> NUMBER OF SEQ ID NOS: 51

<210> SEQ ID NO 1
<211> LENGTH: 454
<212> TYPE: PRT
<213> ORGANISM: Nannochloropsis oculata NIES2145

<400> SEQUENCE: 1

Met Arg Val Ser Ser Ala Val Leu Gly Cys Ala Leu Leu Phe Ile
1               5                   10                  15

Ala Pro Thr Leu Ala Tyr Leu Pro Thr Asn Val Arg Ala Ser Lys Gly
                20                  25                  30

Arg Ile Tyr Met Lys Glu Lys Thr Gln Arg Val Val Thr Gly Leu
            35                  40                  45

Gly Pro Ile Ser Ala Val Gly Ile Gly Lys Asp Asp Phe Trp Lys Ala
        50                  55                  60

Leu Leu Glu Gly Lys Cys Gly Ile Asp Lys Ile Ser Gly Phe Asp Pro
65                  70                  75                  80

Ser Gly Leu Thr Cys Gln Ile Gly Ala Glu Val Lys Gly Phe Asp Ala
                85                  90                  95

Lys Pro Tyr Phe Lys Asp Lys Lys Ser Ala Val Arg Asn Asp Arg Val
                100                 105                 110

Thr Leu Met Gly Val Ala Ala Ser Arg Ile Ala Val Asp Asp Ala Arg
            115                 120                 125

Leu Asp Leu Ala Thr Val Glu Gly Gly Arg Phe Gly Val Val Val Gly
        130                 135                 140

Ser Ala Phe Gly Gly Leu Gln Thr Leu Glu Thr Gln Ile Gln Ser Met
145                 150                 155                 160

Asn Glu Lys Gly Pro Gly Ala Val Ser Pro Phe Ala Val Pro Met Leu
                165                 170                 175

Leu Ser Asn Leu Ile Ser Gly Val Ile Ala Leu Glu Asn Gly Ala Lys
            180                 185                 190

Gly Pro Asn Tyr Val Val Asn Ser Ala Cys Ala Ala Ser Thr His Ala
        195                 200                 205

Leu Gly Leu Ala Tyr Ala His Ile Ala His Gly Glu Ala Asp Val Cys
    210                 215                 220

Leu Ala Gly Gly Ala Glu Ala Ala Val Thr Pro Phe Gly Tyr Ala Gly
225                 230                 235                 240

Phe Cys Ser Met Lys Ala Met Ala Thr Lys Tyr Asn Asp Asn Pro Ser
                245                 250                 255

Gln Gly Ser Arg Pro Phe Asp Lys Asp Arg Cys Gly Phe Val Met Gly
            260                 265                 270

Glu Gly Ala Gly Met Leu Val Leu Glu Ser Leu Glu His Ala Gln Lys
        275                 280                 285

Arg Gly Ala His Ile Tyr Ala Glu Val Ala Gly Phe Gly Gln Ala Cys
    290                 295                 300

Asp Ala His His Ile Thr Thr Pro His Pro Glu Gly Ala Gly Leu Ala
```

Lys Ala Ile Thr Leu Ala Leu Asp Asp Ala Gly Leu Asp Lys Gly Asp
305                 310                 315                 320

Leu Thr Tyr Ile Asn Ala His Gly Thr Ser Thr Ala Tyr Asn Asp Lys
            325                 330                 335

Phe Glu Thr Leu Ala Val Lys Lys Ala Leu Gly Glu Glu Asn Ala Lys
        340                 345                 350

Arg Met Tyr Leu Ser Ser Thr Lys Gly Ser Thr Gly His Thr Leu Gly
    355                 360                 365

Ala Ala Gly Gly Leu Glu Ala Ile Ala Thr Val Leu Ala Ile Glu Thr
370                 375                 380

Leu Thr Leu Pro Pro Thr Ile Asn Tyr Glu Thr Pro Asp Pro Asp Cys
385                 390                 395                 400

Asp Leu Asn Val Val Pro Asn Lys Pro Ile Lys Val Ala Glu Ile Lys
            405                 410                 415

Ala Ala Ala Ser Gln Ser Ala Gly Phe Gly Gly His Asp Ser Val Val
        420                 425                 430

Ile Phe Lys Pro Phe Lys
    435                 440                 445

450

<210> SEQ ID NO 2
<211> LENGTH: 1365
<212> TYPE: DNA
<213> ORGANISM: Nannochloropsis oculata NIES2145

<400> SEQUENCE: 2
atgcgggtct ccagtagcgc cgttttaggc tgcgccctcc tcttcatcgc cctaccttg      60 gcatacctgc ctaccaacgt gcgcgcctca aagggccgaa tctacatgaa ggagaagacc    120
caacgcgtgg tcgtgacagg cctagggccc atatcggccg tagggatcgg caaggacgat    180
ttctggaagg cgttgctaga ggggaagtgc ggcattgaca agatcagtgg ctttgacct     240 agtggattga cgtgccaaat tggtgcggaa gtgaagggt ttgatgcgaa gccgtatttt     300
aaggacaaga aaagcgccgt ccgtaacgac cgtgtgacac tgatgggggt ggccgcttca    360
agaatcgccg ttgatgatgc caggctggac ttggccacag tggaaggaga gcgcttcggc    420
gtggtggtgg gctccgcttt tgggggcctg caaacgctcg acgcagat tcagagcatg      480 aatgagaagg gcccggggc tgtgtcgccc ttgcggttc ccatgttgtt gtccaacttg      540
atctcgggcg tgattgcctt ggagaacggg gcaaaggac cgaactacgt ggtgaatagc    600
gcgtgtgccg cctcgaccca tgccctcggt ctggcgtacg cccatatcgc gcacggggag   660
gcggatgtct gcttggccgg cggggcggag gctgccgtga caccgttcgg gtacgcgggg   720
ttttgctcca tgaaagccat ggcgaccaaa tacaacgaca cccctccca aggctcccgt     780 cccttcgaca aggatcggtg cggctttgtc atgggcgagg gtgccggtat gctcgtcctc   840
gaatctctcg aacacgccca aaaacgcggc gcgcacatct atgccgaagt cgccggcttt   900
ggtcaggcct gtgacgccca ccatatcacg acccctcacc ccgagggggc gggtctggcg   960
aaagccatca ccttggcatt ggatgacgcg ggcttggaca aggtgattt aacgtacatc    1020 aacgcccatg gcaccagcac ggcgtacaac gacaagttcg agacgttggc ggtcaagaag   1080
gccttggggg aggagaacgc caagaggatg tatttatcgt cgaccaaggg gtcgacggga  1140
cacacgctcg gggccgcggg agggttggag gcgattgcga cagtactagc gattgagacg   1200
ttgaccttgc ccccaccat caactatgag acaccagacc cggactgtga cctgaatgtg    1260

```
gttcccaaca aacccattaa agtggcggag atcaaagccg ctgcttctca gtcggcaggg    1320
tttggagggc atgactcggt tgtaatcttc aaaccgttca gtaa                     1365
```

<210> SEQ ID NO 3
<211> LENGTH: 458
<212> TYPE: PRT
<213> ORGANISM: Nannochloropsis gaditana CCMP526

<400> SEQUENCE: 3

```
Met Arg Leu Ser Thr Leu Ser Val Leu Gly Pro Ala Leu Gly Cys Ala
1               5                   10                  15

Phe Leu Leu Phe Asp Ser Ser Leu Ala Tyr Leu Pro Ser Tyr Met Arg
            20                  25                  30

Gly Ser Lys Gly Gln Ile Tyr Met Lys Glu Lys Ser Gln Arg Val Val
        35                  40                  45

Val Thr Gly Leu Gly Pro Ile Ser Ala Val Gly Ile Gly Lys Asp Ala
    50                  55                  60

Phe Trp Lys Ala Leu Leu Glu Gly Lys Ser Gly Ile Asp Arg Ile Ser
65                  70                  75                  80

Gly Phe Asp Pro Ser Gly Leu Thr Cys Gln Ile Gly Ala Glu Val Lys
                85                  90                  95

Asp Phe Asp Ala Lys Pro Tyr Phe Lys Asp Arg Lys Ser Ala Val Arg
            100                 105                 110

Asn Asp Arg Val Thr Leu Met Gly Val Ala Ala Ser Arg Ile Ala Val
        115                 120                 125

Asp Asp Ala Lys Leu Asp Leu Ser Ser Val Glu Gly Glu Arg Phe Gly
    130                 135                 140

Val Val Val Gly Ser Ala Phe Gly Gly Leu Gln Thr Leu Glu Thr Gln
145                 150                 155                 160

Ile Gln Thr Met Asn Glu Lys Gly Pro Gly Ser Val Ser Pro Phe Ala
                165                 170                 175

Val Pro Ser Leu Leu Ser Asn Leu Ile Ser Gly Val Ile Ala Leu Glu
            180                 185                 190

Asn Gly Ala Lys Gly Pro Asn Tyr Val Val Asn Ser Ala Cys Ala Ala
        195                 200                 205

Ser Thr His Ala Leu Gly Leu Ala Tyr Ala His Ile Ala His Gly Glu
    210                 215                 220

Ala Asp Val Cys Leu Ala Gly Gly Ser Glu Ala Ala Val Thr Pro Phe
225                 230                 235                 240

Gly Phe Ala Gly Phe Cys Ser Met Lys Ala Met Ala Thr Lys Tyr Asn
                245                 250                 255

Asp Asn Pro Ser Gln Gly Ser Arg Pro Phe Asp Lys Asp Arg Cys Gly
            260                 265                 270

Phe Val Met Gly Glu Gly Ala Gly Met Val Val Leu Glu Ser Leu Glu
        275                 280                 285

His Ala Gln Lys Arg Gly Ala His Ile Tyr Ala Glu Val Ala Gly Phe
    290                 295                 300

Gly Gln Ala Cys Asp Ala His His Ile Thr Thr Pro His Pro Glu Gly
305                 310                 315                 320

Ala Gly Leu Ala Gln Ala Ile Thr Leu Ala Leu Glu Asp Ala Gly Met
                325                 330                 335

Ala Lys Glu Asp Leu Thr Tyr Ile Asn Ala His Gly Thr Ser Thr Ala
            340                 345                 350

Tyr Asn Asp Lys Phe Glu Thr Leu Ala Val Lys Lys Ala Leu Gly Glu
```

```
                355                 360                 365
Glu Val Ala Lys Lys Met Tyr Leu Ser Ser Thr Lys Gly Ser Thr Gly
    370                 375                 380

His Thr Leu Gly Ala Ala Gly Gly Leu Glu Ala Ile Ala Thr Val Leu
385                 390                 395                 400

Ala Ile Glu Thr Lys Thr Leu Pro Pro Thr Ile Asn Tyr Glu Thr Pro
                405                 410                 415

Asp Pro Asp Cys Asp Leu Asn Val Val Pro Asn Lys Pro Ile Thr Leu
                420                 425                 430

Asn Glu Ile Thr Gly Ala Ala Ser Gln Ser Ala Gly Phe Gly Gly His
                435                 440                 445

Asp Ser Val Val Val Phe Lys Pro Phe Lys
450                 455

<210> SEQ ID NO 4
<211> LENGTH: 1377
<212> TYPE: DNA
<213> ORGANISM: Nannochloropsis gaditana CCMP526

<400> SEQUENCE: 4
atgcggcttt cgactctcag cgtcttgggc cctgcactag gatgcgcctt cctactattc     60
gattcaagcc tggcatatct accgagctat atgcgtgggt ctaagggaca atctatatg    120 aaggaaaaaa gtcagcgtgt cgtcgtaacg ggtcttggac ccatatccgc tgtgggtatt    180
gggaaagatg ccttctggaa agcgctgttg aagggaaaaa gtggtatcga tcgcatcagc    240
ggctttgacc cctccggcct cacttgccag attggcgccg aagtaaaaga tttcgatgcc    300
aagccttatt tcaaggatag gaagagcgca gttcgtaacg acagggtgac cttgatggga    360
gtggccgcct cgcgcattgc tgtggacgat gccaagctgg atttgtcgtc ggtggagggg    420
gaacgcttcg gggttgtggt agggtccgcg ttcgagggc ttcaaacgct tgagacccag    480
attcagacca tgaacgaaaa gggtccgggc tccgtgtctc ccttcgccgt gccaagtttg    540
ttgtccaact tgatttcggg ggtgattgcg ttggaaaatg gcgcgaaagg ccccaactac    600
gtcgtgaaca gcgcctgtgc cgcgtccacc cacgccctgg ggctggccta cgcacacatt    660
gcccacggag aggcggacgt gtgcctggcg ggcgggtcgg aagcggctgt gaccccgttc    720
ggattcgcgg gcttttgctc gatgaaagcc atggccacaa agtacaatga caaccccagc    780
caaggctccc gacctttcga taaggaccgt tgcggttttg tcatgggaga ggggcccggg    840
atggtggtgc tggaaagctt ggagcatgcg cagaaacggg gcgcgcatat ttacgccgag    900
gtggcgggct ttgggcaggc gtgcgacgcc caccatatca ccactccgca ccctgaggga    960
gcgggcttgg cccaggcaat cacgttggca ttggaggacg cgggtatggc gaaagaggac   1020
ttgacctaca ttaatgccca tggcaccagc accgcctaca tgacaaaatt cgagacgctg   1080
gcggtcaaga aggccttggg agaggaggtg ccaaaaaga tgtacttgtc gtcgaccaag   1140
ggatcgacgg gccacacgct gggagcggcg ggtggactag aagcaatcgc gacagtcctg   1200
gccatagaga cgaagacact gccgcctacg atcaattacg agacgcctga cccggattgc   1260
gacctaaacg tagtgccgaa caagcccatc accctgaatg agatcacagg ggccgcctct   1320
cagtccgctg gcttcggcgg cgcatgactcg gtggtggtgt tcaaaccatt caaataa     1377

<210> SEQ ID NO 5
<211> LENGTH: 303
<212> TYPE: PRT
<213> ORGANISM: Cocos nucifera
```

<400> SEQUENCE: 5

| Leu | Asp | Ser | Lys | Lys | Arg | Gly | Ala | Asp | Ala | Val | Ala | Asp | Ala | Ser | Gly |
| 1 | | | | 5 | | | | | 10 | | | | | 15 | |

| Val | Gly | Lys | Met | Val | Lys | Asn | Gly | Leu | Val | Tyr | Arg | Gln | Asn | Phe | Ser |
| | | | 20 | | | | | 25 | | | | | 30 | | |

| Ile | Arg | Ser | Tyr | Glu | Ile | Gly | Val | Asp | Lys | Arg | Ala | Ser | Val | Glu | Ala |
| | | 35 | | | | | 40 | | | | | 45 | | | |

| Leu | Met | Asn | His | Phe | Gln | Glu | Thr | Ser | Leu | Asn | His | Cys | Lys | Cys | Ile |
| | 50 | | | | | 55 | | | | | 60 | | | | |

| Gly | Leu | Met | His | Gly | Gly | Phe | Gly | Cys | Thr | Pro | Glu | Met | Thr | Arg | Arg |
| 65 | | | | 70 | | | | | 75 | | | | | 80 | |

| Asn | Leu | Ile | Trp | Val | Val | Ala | Lys | Met | Leu | Val | His | Val | Glu | Arg | Tyr |
| | | | 85 | | | | | 90 | | | | | 95 | | |

| Pro | Trp | Trp | Gly | Asp | Val | Val | Gln | Ile | Asn | Thr | Trp | Ile | Ser | Ser | Ser |
| | | | 100 | | | | | 105 | | | | | 110 | | |

| Gly | Lys | Asn | Gly | Met | Gly | Arg | Asp | Trp | His | Val | His | Asp | Cys | Gln | Thr |
| | | 115 | | | | | 120 | | | | | 125 | | | |

| Gly | Leu | Pro | Ile | Met | Arg | Gly | Thr | Ser | Val | Trp | Val | Met | Met | Asp | Lys |
| | 130 | | | | | 135 | | | | | 140 | | | | |

| His | Thr | Arg | Arg | Leu | Ser | Lys | Leu | Pro | Glu | Glu | Val | Arg | Ala | Glu | Ile |
| 145 | | | | | 150 | | | | | 155 | | | | | 160 |

| Thr | Pro | Phe | Phe | Ser | Glu | Arg | Asp | Ala | Val | Leu | Asp | Asn | Gly | Arg |
| | | | 165 | | | | | 170 | | | | | 175 | |

| Lys | Leu | Pro | Lys | Phe | Asp | Asp | Ser | Ala | Ala | His | Val | Arg | Arg | Gly |
| | | 180 | | | | | 185 | | | | | 190 | | |

| Leu | Thr | Pro | Arg | Trp | His | Asp | Phe | Asp | Val | Asn | Gln | His | Val | Asn | Asn |
| | 195 | | | | | 200 | | | | | 205 | | | | |

| Val | Lys | Tyr | Val | Gly | Trp | Ile | Leu | Glu | Ser | Val | Pro | Val | Trp | Met | Leu |
| 210 | | | | | 215 | | | | | 220 | | | | | |

| Asp | Gly | Tyr | Glu | Val | Ala | Thr | Met | Ser | Leu | Glu | Tyr | Arg | Arg | Glu | Cys |
| 225 | | | | | 230 | | | | | 235 | | | | | 240 |

| Arg | Met | Asp | Ser | Val | Val | Gln | Ser | Leu | Thr | Ala | Val | Ser | Ser | Asp | His |
| | | | 245 | | | | | 250 | | | | | 255 | | |

| Ala | Asp | Gly | Ser | Pro | Ile | Val | Cys | Gln | His | Leu | Leu | Arg | Leu | Glu | Asp |
| | | 260 | | | | | 265 | | | | | 270 | | | |

| Gly | Thr | Glu | Ile | Val | Arg | Gly | Gln | Thr | Glu | Trp | Arg | Pro | Lys | Gln | Gln |
| | 275 | | | | | 280 | | | | | 285 | | | | |

| Ala | Cys | Asp | Leu | Gly | Asn | Met | Gly | Leu | His | Pro | Thr | Glu | Ser | Lys |
| 290 | | | | | 295 | | | | | 300 | | | | | |

<210> SEQ ID NO 6
<211> LENGTH: 912
<212> TYPE: DNA
<213> ORGANISM: Cocos nucifera

<400> SEQUENCE: 6

```
ctcgattcca agaagagggg ggccgacgcg gtcgcagatg cctctggggt cgggaagatg      60
gtcaagaatg gacttgttta caggcagaat ttttctatcc ggtcctacga aatcggggtt     120
gataaacgtg cttcggtaga ggcattgatg aatcatttcc aggaaacgtc gcttaaccat     180
tgcaagtgta ttggccttat gcatggcggc tttggttgta caccagagat gactcgaaga     240
aatctgatat gggttgttgc caaaatgctg gttcatgtcg aacgttatcc ttggtgggga     300
gacgtggttc aaataaatac gtggattagt tcatctggaa agaatggtat gggacgtgat     360
```

```
tggcatgttc atgactgcca aactggccta cctattatga ggggtaccag tgtctgggtc    420
atgatggata aacacacgag gagactgtct aaacttcctg aagaagttag agcagagata    480
accccttct tttcagagcg tgatgctgtt ttggacgata acggcagaaa acttcccaag     540
ttcgatgatg attctgcagc tcatgttcga aggggcttga ctcctcgttg gcatgatttc    600
gatgtaaatc agcatgtgaa caatgtcaaa tacgtcggct ggattcttga gagcgttcct    660
gtgtggatgt tggatggcta cgaggttgca accatgagtc tggaataccg gagggagtgt    720
aggatggata gtgtggtgca gtctctcacc gccgtctctt ccgaccacgc cgacggctcc    780
cccatcgtgt gccagcatct tctgcggctc gaggatggga ctgagattgt gaggggtcaa    840
acagaatgga ggcctaagca gcaggcttgt gatcttggga acatgggtct gcacccaact    900
gagagtaaat ga                                                        912
```

```
<210> SEQ ID NO 7
<211> LENGTH: 287
<212> TYPE: PRT
<213> ORGANISM: Nannochloropsis oculata

<400> SEQUENCE: 7

Met Thr Pro Leu Ala Phe Thr Val Leu Gly Lys Leu Gly Gly Thr Leu
1               5                   10                  15

Thr Phe Ala Cys Val Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Ala Thr Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270
```

Ser Gln Ser Pro Leu Leu Lys Gly Pro Lys Lys Ile Asp Ile Ser
            275                 280                 285

<210> SEQ ID NO 8
<211> LENGTH: 864
<212> TYPE: DNA
<213> ORGANISM: Nannochloropsis oculata

<400> SEQUENCE: 8

```
atgacgcctt tggccttcac ggtgctcggc aagcttggtg gcacgttgac ttttgcttgt     60
gtacgacgga ggctttatca cttgttacgg cgggcaactt tgtcctccca ttatcaggtc    120
actcggcctt acggtcacag caattccggc tgttcacata gcactaccac acttagaacc    180
agcttcccag tcctctttgc gcaattggca gcagccactg ctgccgtcgt cgctgccatt    240
tccctgccgt cgcctagtct atgcgagacg gcccacgccg ggactgagga gagacgaggt    300
gagaggaagg caatgaggga ggatggtgga aaaggcgagg ccacctcgtc tgctacatgc    360
aatccatcct tattcgaaca tcatgatcgc gtcgacacca agctgcatcg ggcctatcct    420
gaattcctga agttccacct tatccacgag acgctccgag gcaaagagaa aattgatggc    480
tacgaagttt acaagacag gcgggatgat tcaattgtgg cgtatgctcg ccttggcaaa    540
ctgctgagcg acaccccga cataatccac ggagggtcca ttgcggcttt gctggacaat    600
accatgggag ttgccttttt cgccgccaag cgtggcaatg ttttacagc aaatctcacc    660
atcaactaca agcgacccat cacgtgtggc accgaagtca agttttagc tcgagtagag    720
aaggtggaag ggcgcaaggt cttcttgcgg gccgagattc gagacgctaa ggatgaggct    780
atcctctaca ctgaagccaa atccctcttc atcacgtctc aaagtccttt attgaagggc    840
ccaaagaaaa ttgatattag ctag                                          864
```

<210> SEQ ID NO 9
<211> LENGTH: 382
<212> TYPE: PRT
<213> ORGANISM: Umbellularia californica

<400> SEQUENCE: 9

Met Ala Thr Thr Ser Leu Ala Ser Ala Phe Cys Ser Met Lys Ala Val
1               5                   10                  15

Met Leu Ala Arg Asp Gly Arg Gly Met Lys Pro Arg Ser Ser Asp Leu
            20                  25                  30

Gln Leu Arg Ala Gly Asn Ala Pro Thr Ser Leu Lys Met Ile Asn Gly
        35                  40                  45

Thr Lys Phe Ser Tyr Thr Glu Ser Leu Lys Arg Leu Pro Asp Trp Ser
    50                  55                  60

Met Leu Phe Ala Val Ile Thr Thr Ile Phe Ser Ala Ala Glu Lys Gln
65                  70                  75                  80

Trp Thr Asn Leu Glu Trp Lys Pro Lys Pro Lys Leu Pro Gln Leu Leu
                85                  90                  95

Asp Asp His Phe Gly Leu His Gly Leu Val Phe Arg Arg Thr Phe Ala
            100                 105                 110

Ile Arg Ser Tyr Glu Val Gly Pro Asp Arg Ser Thr Ser Ile Leu Ala
        115                 120                 125

Val Met Asn His Met Gln Glu Ala Thr Leu Asn His Ala Lys Ser Val
    130                 135                 140

Gly Ile Leu Gly Asp Gly Phe Gly Thr Thr Leu Glu Met Ser Lys Arg
145                 150                 155                 160

```
Asp Leu Met Trp Val Val Arg Arg Thr His Val Ala Val Glu Arg Tyr
                165                 170                 175

Pro Thr Trp Gly Asp Thr Val Glu Val Glu Cys Trp Ile Gly Ala Ser
            180                 185                 190

Gly Asn Asn Gly Met Arg Arg Asp Phe Leu Val Arg Asp Cys Lys Thr
        195                 200                 205

Gly Glu Ile Leu Thr Arg Cys Thr Ser Leu Ser Val Leu Met Asn Thr
    210                 215                 220

Arg Thr Arg Arg Leu Ser Thr Ile Pro Asp Glu Val Arg Gly Glu Ile
225                 230                 235                 240

Gly Pro Ala Phe Ile Asp Asn Val Ala Val Lys Asp Asp Glu Ile Lys
                245                 250                 255

Lys Leu Gln Lys Leu Asn Asp Ser Thr Ala Asp Tyr Ile Gln Gly Gly
                260                 265                 270

Leu Thr Pro Arg Trp Asn Asp Leu Asp Val Asn Gln His Val Asn Asn
            275                 280                 285

Leu Lys Tyr Val Ala Trp Val Phe Glu Thr Val Pro Asp Ser Ile Phe
        290                 295                 300

Glu Ser His His Ile Ser Ser Phe Thr Leu Glu Tyr Arg Arg Glu Cys
305                 310                 315                 320

Thr Arg Asp Ser Val Leu Arg Ser Leu Thr Thr Val Ser Gly Gly Ser
                325                 330                 335

Ser Glu Ala Gly Leu Val Cys Asp His Leu Leu Gln Leu Glu Gly Gly
                340                 345                 350

Ser Glu Val Leu Arg Ala Arg Thr Glu Trp Arg Pro Lys Leu Thr Asp
            355                 360                 365

Ser Phe Arg Gly Ile Ser Val Ile Pro Ala Glu Pro Arg Val
        370                 375                 380

<210> SEQ ID NO 10
<211> LENGTH: 1149
<212> TYPE: DNA
<213> ORGANISM: Umbellularia californica

<400> SEQUENCE: 10
atggccacca cctctcttagc ttccgctttc tgctcgatga aagctgtaat gttggctcgt      60
gatggccggg gcatgaaacc caggagcagt gatttgcagc tgagggcggg aaatgcgcca     120
acctctttga agatgatcaa tgggaccaag ttcagttaca cggagagctt gaaaaggttg     180
cctgactgga gcatgctctt gcagtgatc acaaccatct tttcggctgc tgagaagcag     240
tggaccaatc tagagtggaa gccgaagccg aagctacccc agttgcttga tgaccatttt     300
ggactgcatg gttagttttc aggcgcacc tttgccatca gatcttatga ggtgggacct     360
gaccgctcca catctatact ggctgttatg aatcacatgc aggaggctac acttaatcat     420
gcgaagagtg tgggaattct aggagatgga ttcgggacga cgctagagat gagtaagaga     480
gatctgatgt gggttgtgag acgcacgcat gttgctgtgg aacggtaccc tacttggggt     540
gatactgtag aagtagagtg ctggattggt gcatctggaa ataatggcat gcgacgtgat     600
ttccttgtcc gggactgcaa aacaggcgaa attcttacaa gatgtaccag cctttcggtg     660
ctgatgaata acaggacaag gaggttgtcc acaatccctg acgaagttag aggggagata     720
gggcctgcat tcattgataa tgtggctgtc aaggacgatg aaattaagaa actacagaag     780
ctcaatgaca gcactgcaga ttacatccaa ggaggtttga ctcctcgatg gaatgatttg     840
```

| | |
|---|---:|
| gatgtcaatc agcatgtgaa caacctcaaa tacgttgcct gggttttttga gaccgtccca | 900 |
| gactccatct ttgagagtca tcatatttcc agcttcactc ttgaatacag gagagagtgc | 960 |
| acgagggata gcgtgctgcg gtccctgacc actgtctctg gtggctcgtc ggaggctggg | 1020 |
| ttagtgtgcg atcacttgct ccagcttgaa ggtgggtctg aggtattgag ggcaagaaca | 1080 |
| gagtggaggc ctaagcttac cgatagtttc agagggatta gtgtgatacc cgcagaaccg | 1140 |
| agggtgtaa | 1149 |

<210> SEQ ID NO 11
<211> LENGTH: 274
<212> TYPE: PRT
<213> ORGANISM: Nannochloropsis gaditana

<400> SEQUENCE: 11

```
Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205

Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser
```

<210> SEQ ID NO 12
<211> LENGTH: 825
<212> TYPE: DNA
<213> ORGANISM: Nannochloropsis gaditana

<400> SEQUENCE: 12

```
atgctatgtt gcgcctgtaa atcagtgcat gcgactatta gtgtcgcctt tattggtact      60
cggaagccac atcgtttgcc tgcattgttt ccattgttcc ttgccccggc ccgagcactc     120
agccatcagg agccgaaccc tgcaacgtgc gggacgcaaa actcatcctt ctcgatcttg     180
ttgaaaacgg tagtagcagg atcattcgtc ggtgcggcat tcatcgctgg catacagca     240
ggggctagct gtgatgaagt aaagtctccg caggaggtga acaatgtagg aggcggcgcc     300
ccagtgactg cccctacac ggtcactttt gcgtccaatt atcatgatcg agtggacaca     360
aaacttcata gagcttatcc tgagttttta cagtaccatc ttattcatga aacgcttcga     420
ggcaaggaaa agatagaggg ctacgaggtg tacaaagata ggcgtgacga ttctatcgta     480
gcatttgctc gcctcgggaa gcttctcagc gggcatccgg atataatcca tggaggctct     540
atagccgcct tactcgacaa cactatgggc gtggcattct tcgctgccaa taaaggtaat     600
ggcttcactg ccaacctcac aatcaattac aagaggccga tcatttgtgg caccgagatc     660
aaggtcttgg cccgagtgga gcggtttgaa ggacgcaagg ttttcctacg agcagagatt     720
cgagatgcta aggacgaggc agtgttgtac acggaagcca catccctctt cataacttca     780
caaagtcctc tgcttacggg accgaagaag gtggacatca gttag                    825
```

<210> SEQ ID NO 13
<211> LENGTH: 285
<212> TYPE: PRT
<213> ORGANISM: Nannochloropsis granulata

<400> SEQUENCE: 13

```
Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220
```

```
Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
            245                 250                 255

Glu Ala Ile Leu Tyr Thr Glu Ala Asn Ser Leu Phe Ile Thr Ser Gln
        260                 265                 270

Ser Pro Leu Leu Lys Gly Pro Lys Lys Ile Asp Ile Ser
    275                 280                 285
```

<210> SEQ ID NO 14
<211> LENGTH: 858
<212> TYPE: DNA
<213> ORGANISM: Nannochloropsis granulata

<400> SEQUENCE: 14

```
atgacgcctt tggccttcac ggcgctcggc gaggtcggtg catgttggc tgctgcctgt      60
gtacgacgga agcttcatca cttgttgcgg cgggcagctt cgtcctccca ggtcactcga    120
ccttacagtc acagcaccgc caacagcaca catagcacca ccacacttag caacagcttt    180
ccagtcctct tgcgcaact cgcagcagcc gctgctgccg tcatggctgc cacttccctg     240
tcgtcgccca gtctatgtga cggcccac accaatactg aggagagagg aggcgaaggg      300
gaggcaatga gggagaaggg tggggaaggc gaggccactt cgtctgctac atgcgctcca    360
tctttcttcg agcatcatga tcgcgtcgac acgaagctgc atcgggccta tcccgagttt    420
ctgaagttcc acctcatcca cgagacgctc cgagggaaag agaaaattga tggctacgaa    480
gtatacaaaa acaggcggga cgattcagtt gtggcgtatg ctcgcctggg caaactgctg    540
agcggacacc ctgacataat tcacggaggg tccatcgctg ctttgctgga acaccatg     600
ggagttgcct ttttcgccgc caagcgcggc aatggtttca gcaaatctca ccatcaac    660
tacaagcgac ccatcacgtg tggcaccgag gtcaaagttc tggctcgagt agagaaggtg    720
gaggggcgca aggtcttttt gcgggctgag atcagggacg ccaaggatga ggctatcctt    780
tacactgaag ccaactccct cttcatcacg tcgcaaagcc ctctattgaa gggcccaaag    840
aaaattgaca ttagctag                                                  858
```

<210> SEQ ID NO 15
<211> LENGTH: 233
<212> TYPE: PRT
<213> ORGANISM: Symbiodinium microadriaticum

<400> SEQUENCE: 15

```
Met Ala Phe Arg Leu Cys Ser Leu Ser Arg Arg Phe Ala Ala His Ala
1               5                   10                  15

Gln Gln Val Leu Arg Lys Glu Ala Gly Phe Glu Phe Arg Ala Ser Cys
            20                  25                  30

Ile Ala Ile Thr Ala Gly Ile Ser Ala Gly Trp Cys Met Gln Gln Ala
        35                  40                  45

Ala Arg Ala Glu Gly Ile Trp Thr Pro His Leu Gly Glu Glu Ala Lys
    50                  55                  60

Leu Leu Asn Leu Gln Arg Glu Met Ala Leu Arg Asp Arg His Asp Lys
65                  70                  75                  80

Gln Phe Val Trp Gln Thr Cys Ser Gly Gln Gly Lys Ile Glu Asp Cys
                85                  90                  95

Arg Ile Tyr His Cys Lys Arg Glu Glu Val Asp Arg Glu Val Ser Leu
            100                 105                 110
```

```
Asp Ala Pro Glu Met Val Glu Gly Lys Thr Arg Ile Cys Ala Val Met
        115                 120                 125

Arg Val Gly Asp Glu Leu Asn Gly His Pro Gly Leu Leu His Gly Gly
    130                 135                 140

Phe Thr Ala Ala Val Leu Asp Asp Phe Thr Gly Leu Ala Thr Trp Met
145                 150                 155                 160

Glu Lys Gln Ala Gln Ala Leu Asp Lys Asp Ala Ala Ile Phe Thr Ala
                165                 170                 175

His Met Asp Leu Ser Tyr Arg Arg Pro Leu Lys Ala Lys Ser Glu Tyr
            180                 185                 190

Leu Val Glu Val Cys Val Asp Arg Val Glu Arg Gln Lys Lys Val Phe
        195                 200                 205

Leu Asn Ala Ala Ile Tyr Asp Lys Asp Ser His Ala Cys Val Lys Ala
    210                 215                 220

Lys Val Leu Tyr Ile Val Lys Lys Lys
225                 230
```

<210> SEQ ID NO 16
<211> LENGTH: 702
<212> TYPE: DNA
<213> ORGANISM: Symbiodinium microadriaticum

<400> SEQUENCE: 16

```
atggctttca ggctatgctc tctttcccgg cggtttgctg cgcacgcgca gcaggtgctg      60
cggaaggagg ctggctttga gttccgcgca agctgcatcg ccattaccgc tggcatctct     120
gctggatggt gcatgcagca ggcagcgcgg gcggagggca tctggactcc gcacctgggc     180
gaggaggcca gttgttgaa cctccagcgc gagatggcgc tgagagacag acacgacaag     240
caatttgtgt ggcagacctg cagtggccag ggcaaaattg aggactgccg catatatcac     300
tgcaagcgag aagaagttga tcgtgaggtt tcgctggacg cgccggaaat ggtggagggc     360
aaaacacgga tttgtgcagt gatgcgcgtt ggcgacgagc tgaacggcca tcctgggctt     420
ttgcatggcg gcttcactgc cgccgtgctg gacgatttca caggcctggc gacctggatg     480
gagaagcaag cgcaggcgct ggacaaggat gcggccattt tcaccgctca catggatctc     540
agctatcggc gacccctgaa ggcgaagtcg gagtacttgg ttgaggtttg cgttgaccgt     600
gttgagcggc aaaagaaggt cttctctgaat gctgccatct atgacaagga cagccatgcc     660
tgcgtgaaag caaaggtgtt gtacatcgtc aaaaagaagt ga                        702
```

<210> SEQ ID NO 17
<211> LENGTH: 1158
<212> TYPE: DNA
<213> ORGANISM: Enterococcus faecalis

<400> SEQUENCE: 17

```
atcgattttc gttcgtgaat acatgttata ataactataa ctaataacgt aacgtgactg      60
gcaagagata ttttttaaaac aatgaatagg tttacactta ctttagtttt atggaaatga    120
aagatcatat catatataat ctagaataaa attaactaaa ataattatta tctagataaa    180
aaatttagaa gccaatgaaa tctataaata aactaaatta agtttattta attaacaact    240
atggatataa ataggtact aatcaaaata gtgaggagga tatatttgaa tacatacgaa     300
caaattaata aagtgaaaaa atacttcgg aaacatttaa aaaataaacct tattggtact    360
tacatgtttg gatcaggagt tgagagtgga ctaaaaccaa atagtgatct tgactttttta    420
```

```
gtcgtcgtat ctgaaccatt gacagatcaa agtaaagaaa tacttataca aaaaattaga      480
cctatttcaa aaaaaatagg agataaaagc aacttacgat atattgaatt aacaattatt      540
attcagcaag aaatggtacc gtggaatcat cctcccaaac aagaatttat ttatggagaa      600
tggttacaag agctttatga acaaggatac attcctcaga aggaattaaa ttcagattta      660
accataatgc tttaccaagc aaaacgaaaa aataaaagaa tatacggaaa ttatgactta      720
gaggaattac tacctgatat tccatttttct gatgtgagaa gagccattat ggattcgtca      780
gaggaattaa tagataatta tcaggatgat gaaaccaact ctatattaac tttatgccgt      840 atgatttttaa ctatggacac gggtaaaatc ataccaaaag atattgcggg aaatgcagtg      900
gctgaatctt ctccattaga acataggggag agaattttgt tagcagttcg tagttatctt      960
ggagagaata ttgaatggac taatgaaaat gtaaatttaa ctataaacta tttaaataac     1020
agattaaaaa aattataaaa aaattgaaaa aatggtggaa acactttttt caattttttt     1080
gttttattat ttaatatttg ggaaatattc attctaattg gtaatcagat tttagaaaac     1140 aataaacccct tgcatatg                                                  1158

<210> SEQ ID NO 18
<211> LENGTH: 236
<212> TYPE: DNA
<213> ORGANISM: Synechococcus elongatus sp.

<400> SEQUENCE: 18
ctggatttag cgtcttctaa tccagtgtag acagtagttt tggctccgtt gagcactgta       60
gccttgggcg atcgctctaa acattacata aattcacaaa gttttcgtta cataaaaata      120
gtgtctactt agctaaaaat taagggtttt ttacaccttt ttgacagtta atctcctagc      180
ctaaaaagca agagttttta actaagactc ttgcccttta caacctcaag atcgat         236

<210> SEQ ID NO 19
<211> LENGTH: 1149
<212> TYPE: DNA
<213> ORGANISM: Umbellularia californica

<400> SEQUENCE: 19
atggctacca cctctcttagc ttccgccttt tgctcgatga aagctgtaat gttagctcgt       60
gatggtcggg gtatgaaacc tcgtagtagt gatttgcaac tccgtgcggg aaatgcgcct      120
acctctttga aaatgatcaa tgggaccaaa ttcagttata cggagagctt gaaacggttg      180
cctgattgga gcatgctctt tgctgttatc accaccatct tttcggctgc tgagaaacaa      240
tggactaatc tagagtggaa gccgaaaccg aagctacccc agttgcttga tgatcatttt      300
ggactgcatg ggttagtttt ccggcgcacc tttgccatcc ggtcttatga agttggacct      360
gatcgctcca cctctattct ggctgttatg aatcatatgc aggaggctac ccttaatcat      420
gcgaaaagtg tgggaattct aggagatgga ttcgggacga cgctagagat gagtaagcgg      480
gatctgatgt gggttgttcg gcgcacgcat gttgctgttg aacggtaccc tacttggggt      540
gatactgtag aagtagagtg ctggattggt gcttctggaa ataatggcat gcgtcgtgat      600
ttccttgtcc gggactgcaa aaccggcgaa attcttactc gctgtaccag cctttcggtg      660
ctgatgaata ctcgcactcg tcgtttgtcc accattcctg atgaagttcg tggtgaaata      720
gggcctgctt tcatcgataa tgttgctgtg aaagacgatg aaattaagaa actacaaaaa      780
ctcaatgata gcactgccga ttatattcaa ggaggtttga ccccctcgttg gaatgatttg      840 gatgtcaatc aacatgttaa caacctcaaa tacgttgcct gggttttttga accgtcccc      900
```

```
gattccatct tgagagtca tcatatttcc agcttcactc ttgaatatcg tcgtgagtgt    960
acccgtgata gcgtgctgcg gtccctgacc actgtctctg gtggctcgtc ggaggctggg   1020
ttagtttgcg atcatttgct ccaacttgaa ggtgggtctg aggtattgcg tgccagaact   1080
gagtggcggc ctaaacttac cgatagtttc cgcggcatta gtgttattcc cgccgaaccg   1140
cgcgtgtaa                                                           1149
```

<210> SEQ ID NO 20
<211> LENGTH: 798
<212> TYPE: DNA
<213> ORGANISM: Synechococcus elongatus sp.

<400> SEQUENCE: 20

```
aatgccttct ccaagggcgg cattcccctg actgttgaag gcgttgccaa tatcaagatt     60
gctggggaag aaccgaccat ccacaacgcg atcgagcggc tgcttggcaa aaaccgtaag    120
gaaatcgagc aaattgccaa ggagacccte gaaggcaact tgcgtggtgt tttagccagc    180
ctcacgccgg agcagatcaa cgaggacaaa attgcctttg ccaaaagtct gctggaagag    240
gcggaggatg accttgagca gctgggtcaa gtcctcgata cgctgcaagt ccagaacatt    300
tccgatgagg tcggttatct ctcggctagt ggacgcaagc agcgggctga tctgcagcga    360
gatgcccgaa ttgctgaagc cgatgcccag gctgcctctg cgatccaaac ggccgaaaat    420
gacaagatca cggccctgcg tcggatcgat cgcgatgtag cgatcgccca gccgaggcc     480 gagcgccgga ttcaggatgc gttgacgcgg cgcgaagcgg tggtgccgga agctgaagcg    540
gacattgcta ccgaagtcgc tcgtagccaa gcagaactcc ctgtgcagca ggagcggatc    600
aaacaggtgc agcagcaact tcaagccgat gtgatcgccc cagctgaggc agcttgtaaa    660
cgggcgatcg cggaagcgcg gggggccgcc gcccgtatcg tcgaagatgg aaaagctcaa    720
gcggaaggga cccaacggct ggcggaggct tggcagaccg ctggtgctaa tgcccgcgac    780
atcttcctgc tccagaag                                                 798
```

<210> SEQ ID NO 21
<211> LENGTH: 781
<212> TYPE: DNA
<213> ORGANISM: Synechococcus elongatus sp.

<400> SEQUENCE: 21

```
tcgagtccct gctcgtcacg ctttcaggca ccgtgccaga tatcgacgtg gagtcgatca     60
ctgtgattgg cgaaggggaa ggcagcgcta cccaaatcgc tagcttgctg gagaagctga    120
aacaaaccac gggcattgat ctggcgaaat ccctaccggg tcaatccgac tcgcccgctg    180
cgaagtccta agagatagcg atgtgaccgc gatcgcttgt caagaatccc agtgatcccg    240
aaccatagga aggcaagctc aatgcttgcc tcgtcttgag gactatctag atgtctgtgg    300
aacgcacatt tattgccatc aagcccgatg gcgttcagcg gggtttggtc ggtacgatca    360
tcggccgctt tgagcaaaaa ggcttcaaac tggtgggcct aaagcagctg aagcccagtc    420
gcgagctggc cgaacagcac tatgctgtcc accgcgagcg ccccttcttc aatggcctcg    480
tcgagttcat cacctctggg ccgatcgtgg cgatcgtctt ggaaggcgaa ggcgttgtgg    540
cggctgctcg caagttgatc ggcgctacca atccgctgac ggcagaaccg gccaccatcc    600
gtggtgattt tggtgtcaat attggccgca acatcatcca tggctcggat gcaatcgaaa    660
cagcacaaca ggaaattgct ctctggttta gcccagcaga gctaagtgat tggaccccca    720
```

```
cgattcaacc ctggctgtac gaataaggtc tgcattcctt cagagagaca ttgccatgcc    780
g                                                                   781
```

```
<210> SEQ ID NO 22
<211> LENGTH: 1489
<212> TYPE: DNA
<213> ORGANISM: Enterococcus faecalis

<400> SEQUENCE: 22
gataaaccca gcgaaccatt tgaggtgata ggtaagatta taccgaggta tgaaaacgag     60
aattggacct ttacagaatt actctatgaa gcgccatatt taaaaagcta ccaagacgaa    120
gaggatgaag aggatgagga ggcagattgc cttgaatata ttgacaatac tgataagata    180
atatatcttt tatatagaag atatcgccgt atgtaaggat ttcaggggc aaggcatagg    240 cagcgcgctt atcaatatat ctatagaatg ggcaaagcat aaaaacttgc atggactaat    300
gcttgaaacc caggacaata accttatagc ttgtaaattc tatcataatt gtggtttcaa    360
aatcggctcc gtcgatacta tgttatacgc caactttcaa acaactttg aaaaagctgt    420 tttctggtat ttaaggtttt agaatgcaag gaacagtgaa ttggagttcg tcttgttata    480
attagcttct tggggtatct ttaaatactg tagaaaagag gaaggaaata ataaatggct    540
aaaatgagaa tatcaccgga attgaaaaaa ctgatcgaaa ataccgctg cgtaaaagat    600 acggaaggaa tgtctcctgc taaggtatat aagctggtgg gagaaaatga aacctatat    660 ttaaaaatga cggacagccg gtataaaggg accacctatg atgtggaacg ggaaaaggac    720
atgatgctat ggctggaagg aaagctgcct gttccaaagg tcctgcactt tgaacggcat    780
gatggctgga gcaatctgct catgagtgag gccgatggcg tcctttgctc ggaagagtat    840
gaagatgaac aaagccctga aaagattatc gagctgtatg cggagtgcat caggctcttt    900
cactccatcg acatatcgga ttgtccctat acgaatagct tagacagccg cttagccgaa    960
ttggattact tactgaataa cgatctggcc gatgtggatt gcgaaaactg ggaagaagac   1020
actccattta aagatccgcg cgagctgtat gattttttaa agacggaaaa gcccgaagag   1080
gaacttgtct tttcccacgg cgacctggga gacagcaaca tctttgtgaa agatggcaaa   1140
gtaagtggct ttattgatct tgggagaagc ggcagggcgg acaagtggta tgacattgcc   1200
ttctgcgtcc ggtcgatcag ggaggatatc ggggaagaac agtatgtcga gctatttttt   1260
gacttactgg ggatcaagcc tgattgggag aaaataaaat attatatttt actggatgaa   1320 ttgtttttagt acctagattt agatgtctaa aaagctttaa ctacaagctt tttagacatc   1380
taatcttttc tgaagtacat ccgcaactgt ccatactctg atgttttata tcttttctaa   1440
aagttcgcta gatagggtc ccgagcgcct acgaggaatt tgtatcgat              1489
```

```
<210> SEQ ID NO 23
<211> LENGTH: 147
<212> TYPE: DNA
<213> ORGANISM: Synechococcus elongatus sp.

<400> SEQUENCE: 23
aatttgagcg atcgagaggg tcattgcatc tccagcaaag tcttcaacca ccccaaaacc     60
cagtctccgt ctactcttct gtccatcccg aaaaaatttt tctctgaggg ggttgacgcg    120
actaggcgag ttaggtagat taattaa                                        147
```

```
<210> SEQ ID NO 24
<211> LENGTH: 37
```

<212> TYPE: DNA
<213> ORGANISM: Artificial Sequence
<220> FEATURE:
<223> OTHER INFORMATION: PCR primer, pUC118/0918up-F

<400> SEQUENCE: 24
ggatcctcta gagtcagctc cgttgtcgca gtgtcag                37

<210> SEQ ID NO 25
<211> LENGTH: 38
<212> TYPE: DNA
<213> ORGANISM: Artificial Sequence
<220> FEATURE:
<223> OTHER INFORMATION: PCR primer, 0918down/pUC118-R

<400> SEQUENCE: 25
gcatgcctgc aggtcagaca tcactcaagt catcagtc                38

<210> SEQ ID NO 26
<211> LENGTH: 32
<212> TYPE: DNA
<213> ORGANISM: Artificial Sequence
<220> FEATURE:
<223> OTHER INFORMATION: PCR primer, 0918up/spr-F

<400> SEQUENCE: 26
tcgggcacca caggcatcga ttttcgttcg tg                32

<210> SEQ ID NO 27
<211> LENGTH: 34
<212> TYPE: DNA
<213> ORGANISM: Artificial Sequence
<220> FEATURE:
<223> OTHER INFORMATION: PCR primer, spr/0918down-R

<400> SEQUENCE: 27
aatcggctgg ggttccatat gcaagggttt attg                34

<210> SEQ ID NO 28
<211> LENGTH: 22
<212> TYPE: DNA
<213> ORGANISM: Artificial Sequence
<220> FEATURE:
<223> OTHER INFORMATION: PCR primer, 0918up-R

<400> SEQUENCE: 28
gcctgtggtg cccgaggtat ag                22

<210> SEQ ID NO 29
<211> LENGTH: 22
<212> TYPE: DNA
<213> ORGANISM: Artificial Sequence
<220> FEATURE:
<223> OTHER INFORMATION: PCR primer, 0918down-F

<400> SEQUENCE: 29
gaaccccagc cgattgaaga tg                22

<210> SEQ ID NO 30
<211> LENGTH: 17
<212> TYPE: DNA
<213> ORGANISM: Artificial Sequence
<220> FEATURE:
<223> OTHER INFORMATION: PCR primer, Sp-F

<400> SEQUENCE: 30

-continued atcgattttc gttcgtg    17

<210> SEQ ID NO 31
<211> LENGTH: 38
<212> TYPE: DNA
<213> ORGANISM: Artificial Sequence
<220> FEATURE:
<223> OTHER INFORMATION: PCR primer, 0918up/PpsbA1-F

<400> SEQUENCE: 31
tcgggcacca caggcctgga tttagcgtct tctaatcc    38

<210> SEQ ID NO 32
<211> LENGTH: 38
<212> TYPE: DNA
<213> ORGANISM: Artificial Sequence
<220> FEATURE:
<223> OTHER INFORMATION: PCR primer, PpsbA1/UcTE-R

<400> SEQUENCE: 32
agaggtggta gccatatcga tcttgaggtt gtaaaggg    38

<210> SEQ ID NO 33
<211> LENGTH: 23
<212> TYPE: DNA
<213> ORGANISM: Artificial Sequence
<220> FEATURE:
<223> OTHER INFORMATION: PCR primer, UcTE-F

<400> SEQUENCE: 33
atggctacca cctctttagc ttc    23

<210> SEQ ID NO 34
<211> LENGTH: 34
<212> TYPE: DNA
<213> ORGANISM: Artificial Sequence
<220> FEATURE:
<223> OTHER INFORMATION: PCR primer, UcTE/spr-R

<400> SEQUENCE: 34
gaacgaaaat cgatttacac gcgcggttcg gcgg    34

<210> SEQ ID NO 35
<211> LENGTH: 36
<212> TYPE: DNA
<213> ORGANISM: Artificial Sequence
<220> FEATURE:
<223> OTHER INFORMATION: PCR primer, pUC118/NS1up-F

<400> SEQUENCE: 35
ggatcctcta gagtcaatgc cttctccaag ggcggc    36

<210> SEQ ID NO 36
<211> LENGTH: 37
<212> TYPE: DNA
<213> ORGANISM: Artificial Sequence
<220> FEATURE:
<223> OTHER INFORMATION: PCR primer, NS1up/Kmr-R

<400> SEQUENCE: 36
ttcgctgggt ttatccttct ggagcaggaa gatgtcg    37

<210> SEQ ID NO 37
<211> LENGTH: 36
<212> TYPE: DNA
<213> ORGANISM: Artificial Sequence

```
<220> FEATURE:
<223> OTHER INFORMATION: PCR primer, Kmr/NS1down-F

<400> SEQUENCE: 37
ggaatttgta tcgattcgag tccctgctcg tcacgc                              36

<210> SEQ ID NO 38
<211> LENGTH: 36
<212> TYPE: DNA
<213> ORGANISM: Artificial Sequence
<220> FEATURE:
<223> OTHER INFORMATION: PCR primer, NS1down/pUC118-R

<400> SEQUENCE: 38
gcatgcctgc aggtccggca tggcaatgtc tctctg                              36

<210> SEQ ID NO 39
<211> LENGTH: 18
<212> TYPE: DNA
<213> ORGANISM: Artificial Sequence
<220> FEATURE:
<223> OTHER INFORMATION: PCR primer, Kmr-F

<400> SEQUENCE: 39
gataaaccca gcgaacca                                                  18

<210> SEQ ID NO 40
<211> LENGTH: 18
<212> TYPE: DNA
<213> ORGANISM: Artificial Sequence
<220> FEATURE:
<223> OTHER INFORMATION: PCR primer, Kmr-R

<400> SEQUENCE: 40
atcgatacaa attcctcg                                                  18

<210> SEQ ID NO 41
<211> LENGTH: 22
<212> TYPE: DNA
<213> ORGANISM: Artificial Sequence
<220> FEATURE:
<223> OTHER INFORMATION: PCR primer, NS1up-R

<400> SEQUENCE: 41
cttctggagc aggaagatgt cg                                             22

<210> SEQ ID NO 42
<211> LENGTH: 35
<212> TYPE: DNA
<213> ORGANISM: Artificial Sequence
<220> FEATURE:
<223> OTHER INFORMATION: PCR primer, 0918up/PrrnA-F

<400> SEQUENCE: 42
tcgggcacca caggcaattt gagcgatcga gaggg                               35

<210> SEQ ID NO 43
<211> LENGTH: 37
<212> TYPE: DNA
<213> ORGANISM: Artificial Sequence
<220> FEATURE:
<223> OTHER INFORMATION: PCR primer, PrrnA-R

<400> SEQUENCE: 43
aagggaaaac ctccttggct taattaatct acctaac                             37
```

```
<210> SEQ ID NO 44
<211> LENGTH: 37
<212> TYPE: DNA
<213> ORGANISM: Artificial Sequence
<220> FEATURE:
<223> OTHER INFORMATION: PCR primer, PrrnA/NoKASIV-F

<400> SEQUENCE: 44
aggaggtttt cccttatgcg ggtctccagt agcgccg                                37

<210> SEQ ID NO 45
<211> LENGTH: 39
<212> TYPE: DNA
<213> ORGANISM: Artificial Sequence
<220> FEATURE:
<223> OTHER INFORMATION: PCR primer, NoKASIV/kmr-R

<400> SEQUENCE: 45
ttcgctgggt ttatcttact tgaacggttt gaagattac                              39

<210> SEQ ID NO 46
<211> LENGTH: 1950
<212> TYPE: DNA
<213> ORGANISM: Synechococcus elongatus sp.

<400> SEQUENCE: 46
gtgactggaa ccgccctcgc gcaaccccgc gccattacgc cccacgaaca gcagcttttg        60
gccaaactga aaagctatcg cgatatccaa agcttgtcgc aaatttgggg acgtgctgcc       120
agtcaatttg gatcgatgcc ggctttggtt gcaccccatg ccaaaccagc gatcaccctc       180
agttatcaag aattggcgat tcagatccaa gcgtttgcag ccggactgct cgcgctggga       240
gtgcctacct ccacagccga tgactttccg cctcgcttgg cgcagtttgc ggataacagc       300
ccccgctggt tgattgctga ccaaggcacg ttgctggcag ggctgccaa tgcggtgcgc        360 ggcgcccaag ctgaagtatc ggagctgctc tacgtcttag aggacagcgg ttcgatcggc       420
ttgattgtcg aagacgcggc gctgctgaag aaactacagc ctggtttagc gtcactatcg       480
ctgcagtttg tgatcgtgct cagcgatgaa gtagtcgaga tcgacagcct gcgcgtcgtt       540
ggttttagtg acgtgctgga gatggggcga tcgctgccgg caccggagcc aattttgcag       600
ctcgatcgct tagccacttt tgatctatac ctcgggcacca caggcccacc gaagggcgtg      660
atgctttctc acggcaacct gctgcaccaa gtcacaacat taggtgtggt tgtgcagccg       720
caacctggcg acaccgtgct gagtattttg ccgacttggc actcctacga gcgagcttgt       780
gaatatttcc tgctctccca gggctgcaca caggtctaca cgacgctgcg caatgtcaaa       840
caagacatcc ggcagtatcg gccgcagttc atggtcagtg tgctgcgcct ctgggaatcg       900
atctacgagg gcgtgcagaa gcagtttcgc gagcaaccgg cgaagaaacg tcgcttgatc       960
gataccttct ttggcttgag tcaacgctat gttttggcac ggcgccgctg gcaaggactg      1020
gatttgctgg cactgaacca atccccagcc cagcgcctcg ctgagggtgt ccggatgttg      1080
gcgctagcac cgttgcataa gctgggcgat cgcctcgtct acggcaaagt acgagaagcc      1140
acgggtggcc gaattcggca ggtgatcagt ggcggtggct cactggcact gcacctcgat      1200
accttcttcg aaattgttgg tgttgatttg ctggtgggtt atggcttgac agaaacctca      1260
ccagtgctga cggggcgacg gccttggcac aacctacggg gttcggccgg tcagccgatt      1320
ccaggtacgg cgattcggat cgtcgatcct gaaacgaagg aaaaccgacc cagtggcgat      1380
cgcggcttgg tgctggcgaa agggccgcaa atcatgcagg gctacttcaa taaacccgag      1440
```

```
gcgaccgcga aagcgatcga tgccgaaggt tggtttgaca ccggcgactt aggctacatc    1500
gtcggtgaag gcaacttggt gctaacgggg cgcgctaagg acacgatcgt gctgaccaat    1560
ggcgaaaaca ttgaacccca gccgattgaa gatgcctgcc tacgaagttc ctatatcagc    1620
caaatcatgt tggtgggaca agaccgcaag agtttggggg cgttgattgt gcccaatcaa    1680
gaggcgatcg cactctgggc cagcgaacag gcatcagcc aaaccgatct gcagggagtg    1740
gtacagaagc tgattcgcga ggaactgaac cgcgaagtgc gcgatcgccc gggctaccgc    1800
atcgacgatc gcattggacc attccgcctc atcgaagaac cgttcagcat ggaaaatggc    1860
cagctaaccc aaaccctgaa aatccgtcgc aacgttgtcg cggaacacta cgcggctatg    1920
atcgacggga tgtttgaatc ggcgagttaa                                    1950
```

<210> SEQ ID NO 47
<211> LENGTH: 2864
<212> TYPE: DNA
<213> ORGANISM: Synechococcus elongatus sp.

<400> SEQUENCE: 47

```
agctccgttg tcgcagtgtc agaactcatg gctagcgctc ctcctgaggg ccacacaaag      60
gtgttgatct cactctaggg ggattgggcc gttcctggga atcagtcttg tactacggtt     120
tgtttcaacc gcgatcgcca gccagtttag gccgccgagc cagggcaacg ggcatctgac     180
agcgctgctt gactcacaag aacttgagcc aggctgagac gagcgatcgc ccagtcgcaa     240
aactcccata gcaatgcag ggaatgcgtg atcggtctct aaaatgagga cgctggctga     300
ggagagtaga ccgagtgact ggaaccgccc tcgcgcaacc ccgcgccatt acgccccacg     360
aacagcagct tttggccaaa ctgaaaagct atcgcgatat ccaaagcttg tcgcaaattt     420
ggggacgtgc tgccagtcaa tttggatcga tgccggcttt ggttgcaccc catgccaaac     480
cagcgatcac cctcagttat caagaattgg cgattcagat ccaagcgttt gcagccggac     540
tgctcgcgct gggagtgcct acctccacag ccgatgactt tccgcctcgc ttggcgcagt     600
ttgcggataa cagcccccgc tggttgattg ctgaccaagg cacgttgctg caggggctg      660 ccaatgcggt gcgcggcgcc caagctgaag tatcggagct gctctacgtc ttagaggaca     720
gcggttcgat cggcttgatt gtcgaagacg cggcgctgct gaagaaacta cagcctggtt     780
tagcgtcact atcgctgcag tttgtgatcg tgctcagcga tgaagtagtc gagatcgaca     840
gcctgcgcgt cgttggtttt agtgacgtgc tggagatggg gcgatcgctg ccggcaccgg     900
agccaatttt gcagctcgat cgcttagcca ctttgatcta tacctcgggc accacaggcc     960
caccgaaggg cgtgatgctt tctcacggca acctgctgca ccaagtcaca acattaggtg    1020
tggttgtgca gccgcaacct ggcgacaccg tgctgagtat tttgccgact tggcactcct    1080
acgagcgagc ttgtgaatat ttcctgctct cccagggctg cacacaggtc tacacgacgc    1140
tgcgcaatgt caaacaagac atccggcagt atcggccgca gttcatggtc agtgtgctgc    1200
gcctctggga atcgatctac gagggcgtgc agaagcagtt tcgcgagcaa ccggcgaaga    1260
aacgtcgctt gatcgatacc ttcttttggct tgagtcaacg ctatgttttg gcacggcgcc    1320
gctggcaagg actggatttg ctggcactga accaatcccc agcccagcgc ctcgctgagg    1380
gtgtccggat gttggcgcta gcaccgttgc ataagctggg cgatcgcctc gtctacggca    1440
aagtacgaga agccacgggt ggccgaattc ggcaggtgat cagtggcggt ggctcactgg    1500
cactgcacct cgataccttc ttcgaaattg ttggtgttga tttgctggtg ggttatggct    1560
```

```
tgacagaaac ctcaccagtg ctgacggggc gacggccttg gcacaaccta cggggttcgg      1620
ccggtcagcc gattccaggt acggcgattc ggatcgtcga tcctgaaacg aaggaaaacc      1680
gacccagtgg cgatcgcggc ttggtgctgg cgaaagggcc gcaaatcatg cagggctact      1740
tcaataaacc cgaggcgacc gcgaaagcga tcgatgccga aggttggttt gacaccggcg      1800
acttaggcta catcgtcggt gaaggcaact tggtgctaac ggggcgcgct aaggacacga      1860
tcgtgctgac caatggcgaa acattgaacc ccagccgat tgaagatgcc tgcctacgaa       1920
gttcctatat cagccaaatc atgttggtgg acaagaccg caagagtttg ggggcgttga       1980
ttgtgcccaa tcaagaggcg atcgcactct gggccagcga acagggcatc agccaaaccg      2040
atctgcaggg agtggtacag aagctgattc gcgaggaact gaaccgcgaa gtgcgcgatc      2100
gcccgggcta ccgcatcgac gatcgcattg gaccattccg cctcatcgaa gaaccgttca      2160
gcatggaaaa tggccagcta cccaaaaccc tgaaaatccg tcgcaacgtt gtcgcggaac      2220
actacgcggc tatgatcgac gggatgtttg aatcggcgag ttaagtgtcg attcagcacc      2280
ttgacccttc attcttttct gtgacccctat ctatgaccct cggtactcct ctgcagctaa     2340
agcggacgat caatgtcaaa gcgatcgtga cgccgacttg gaagcaagaa gcccaaaatg      2400
cactgcaggg ccagctcgt caagtggatg cgcagattca acagttggat ttgcaggggc       2460
aagcagcaat caacgaaatt cgcagccaaa gtgccaatcc agtgcatccg aatgtgttgc      2520
aacagattga caacattcag attcaagtca atcagcaaaa aacgcagctg cttgagcaga      2580
agaatcaaat tctccagcaa ctgcaacaag tacaaacggt caacttagaa gaagaagtca      2640
accaaggtca aattgagagc ttcttttgagc tgcatccggg cgataacttg attgaaaaaa     2700
tgcaagttga aatcgtgctg cgcgatggtg ttgttgttga gattcgcggt aatgcttagg      2760
ttttcttgac tcgaccatca atttgtgttg atagctcaca aaaagtttgt gggctttttt      2820
catgcccgtt aagaatactg tgactgatga cttgagtgat gtct                       2864
```

<210> SEQ ID NO 48
<211> LENGTH: 538
<212> TYPE: PRT
<213> ORGANISM: Cuphea lanceolata

<400> SEQUENCE: 48

```
Met Ala Ala Ser Ser Met Ala Ala Ser Pro Phe Cys Thr Trp Leu
1               5                   10                  15

Val Ala Ala Cys Met Ser Thr Ser Phe Glu Asn Asn Pro Arg Ser Pro
            20                  25                  30

Ser Ile Lys Arg Leu Pro Arg Arg Arg Val Leu Ser His Cys Ser
        35                  40                  45

Leu Arg Gly Ser Thr Phe Gln Cys Leu Val Thr Ser His Ile Asp Pro
    50                  55                  60

Cys Asn Gln Asn Cys Ser Ser Asp Ser Leu Ser Phe Ile Gly Val Asn
65                  70                  75                  80

Gly Phe Gly Ser Lys Pro Phe Arg Ser Asn Arg Gly His Arg Arg Leu
                85                  90                  95

Gly Arg Ala Ser His Ser Gly Glu Ala Met Ala Val Ala Leu Gln Pro
            100                 105                 110

Ala Gln Glu Val Ala Thr Lys Lys Pro Ala Ile Lys Gln Arg Arg
        115                 120                 125

Val Val Val Thr Gly Met Gly Val Val Thr Pro Leu Gly His Glu Pro
    130                 135                 140
```

Asp Val Phe Tyr Asn Asn Leu Leu Asp Gly Val Ser Gly Ile Ser Glu
145                 150                 155                 160

Ile Glu Asn Phe Asp Ser Thr Gln Phe Pro Thr Arg Ile Ala Gly Glu
                165                 170                 175

Ile Lys Ser Phe Ser Thr Asp Gly Trp Val Ala Pro Lys Leu Ser Lys
            180                 185                 190

Arg Met Asp Lys Leu Met Leu Tyr Leu Thr Ala Gly Lys Lys Ala
        195                 200                 205

Leu Ala Asp Ala Gly Ile Thr Asp Asp Val Met Lys Glu Leu Asp Lys
    210                 215                 220

Arg Lys Cys Gly Val Leu Ile Gly Ser Gly Met Gly Gly Met Lys Leu
225                 230                 235                 240

Phe Tyr Asp Ala Leu Glu Ala Leu Lys Ile Ser Tyr Arg Lys Met Asn
                245                 250                 255

Pro Phe Cys Val Pro Phe Ala Thr Thr Asn Met Gly Ser Ala Met Leu
                260                 265                 270

Ala Met Asp Leu Gly Trp Met Gly Pro Asn Tyr Ser Ile Ser Thr Ala
            275                 280                 285

Cys Ala Thr Ser Asn Phe Cys Ile Leu Asn Ala Ala Asn His Ile Ile
        290                 295                 300

Arg Gly Glu Ala Asp Met Met Leu Cys Gly Gly Ser Asp Ala Val Ile
305                 310                 315                 320

Ile Pro Ile Gly Leu Gly Gly Phe Val Ala Cys Arg Ala Leu Ser Gln
                325                 330                 335

Arg Asn Asn Asp Pro Thr Lys Ala Ser Arg Pro Trp Asp Ser Asn Arg
            340                 345                 350

Asp Gly Phe Val Met Gly Glu Gly Ala Gly Val Leu Leu Leu Glu Glu
        355                 360                 365

Leu Glu His Ala Lys Lys Arg Gly Ala Thr Ile Tyr Ala Glu Phe Leu
    370                 375                 380

Gly Gly Ser Phe Thr Cys Asp Ala Tyr His Met Thr Glu Pro His Pro
385                 390                 395                 400

Glu Gly Ala Gly Val Ile Leu Cys Ile Glu Lys Ala Met Ala Gln Ala
                405                 410                 415

Gly Val Ser Arg Glu Asp Val Asn Tyr Ile Asn Ala His Ala Thr Ser
            420                 425                 430

Thr Pro Ala Gly Asp Ile Lys Glu Tyr Gln Ala Leu Ala His Cys Phe
        435                 440                 445

Gly Gln Asn Ser Glu Leu Arg Val Asn Ser Thr Lys Ser Met Ile Gly
    450                 455                 460

His Leu Leu Gly Ala Ala Gly Gly Val Glu Ala Val Thr Val Ile Gln
465                 470                 475                 480

Ala Ile Arg Thr Gly Trp Ile His Pro Asn Leu Asn Leu Glu Asp Pro
                485                 490                 495

Asp Lys Ala Val Asp Ala Lys Phe Leu Val Gly Pro Glu Lys Glu Arg
            500                 505                 510

Leu Asn Val Lys Val Gly Leu Ser Asn Ser Phe Gly Phe Gly Gly His
        515                 520                 525

Asn Ser Ser Ile Leu Phe Ala Pro Tyr Asn
    530                 535

<210> SEQ ID NO 49
<211> LENGTH: 1617
<212> TYPE: DNA

<213> ORGANISM: Cuphea lanceolata

<400> SEQUENCE: 49

```
atggcggcgg cctcttccat ggctgcgtca ccgttctgta cgtggctcgt agctgcttgc      60
atgtccactt ccttcgaaaa caacccacgt tcgccctcca tcaagcgtct ccccgccgg      120
aggagggttc tctcccattg ctccctccgt ggatccacct tccaatgcct cgtcacctca     180
cacatcgacc cttgcaatca gaactgctcc tccgactccc ttagcttcat cggggttaac    240
ggattcggat ccaagccatt ccggtccaat cgcggccacc ggaggctcgg ccgtgcttcc    300
cattccgggg aggccatggc tgtggctctg caacctgcac aggaagtcgc cacgaagaag    360
aaacctgcta tcaagcaaag gcgagtagtt gttacaggaa tgggtgtggt gactcctcta    420
ggccatgaac ctgatgtttt ctacaacaat ctcctagatg gagtaagcgg cataagtgag    480
atagagaact tcgacagcac tcagtttccc acgagaattg ccggagagat caagtctttt   540
tccacagatg gctgggtggc cccaaagctc tccaagagga tggacaagct catgctttac    600
ttgttgactc tggcaagaa agcattagca gatgctggaa tcaccgatga tgtgatgaaa    660
gagcttgata aagaaagtg tggagttctc attggctccg gaatgggcgg catgaagttg    720
ttctacgatc gcttgaagc cctgaaaatc tcttacagga agatgaaccc ttttttgtgta    780
ccttttgcca ccacaaatat gggatcagct atgcttgcaa tggatctggg atggatgggt    840
ccaaactact ctatttcaac tgcctgtgca acaagtaatt tctgtatact gaatgctgca    900
aaccacataa tcagaggcga agctgacatg atgctttgtg gtggctcgga tgcggtcatt    960
ataccctatcg gtttgggagg ttttgtggcg tgccgagctt tgtcacagag gaataatgac    1020
cctaccaaag cttcgagacc atgggatagt aatcgtgatg gatttgtaat gggcgaagga   1080
gctggagtgt tacttctcga ggagttagag catgcaaaga aaagaggtgc aaccattat     1140
gcagaattt tagggggcag tttcacttgc gatgcctacc acatgaccga gcctcaccct   1200
gaaggagctg gagtgatcct ctgcatagag aaggccatgg ctcaggccgg agtctctaga   1260
gaagatgtaa attacataaa tgcccatgca acttccactc ctgctggaga tatcaaagaa   1320
taccaagctc tcgcccactg tttcggccaa acagcgagc tgagagtgaa ttccactaaa   1380
tcgatgatcg gtcatcttct tggagcagct ggtggcgtag aagcagttac tgtaattcag   1440
gcgataagga ctgggtggat ccatccaaat cttaatttgg aagacccgga caaagccgtg   1500
gatgcaaaat ttctcgtggg acctgagaag gagagactga atgtcaaggt cggtttgtcc   1560
aattcatttg ggttcggtgg gcataactcg tctatactct cgcccctta caattag       1617
```

<210> SEQ ID NO 50
<211> LENGTH: 37
<212> TYPE: DNA
<213> ORGANISM: Artificial Sequence
<220> FEATURE:
<223> OTHER INFORMATION: primer, PrrnA/ClKASIV-F

<400> SEQUENCE: 50

```
aggaggtttt cccttatggc ggcggcctct tccatgg                              37
```

<210> SEQ ID NO 51
<211> LENGTH: 41
<212> TYPE: DNA
<213> ORGANISM: Artificial Sequence

```
<220> FEATURE:
<223> OTHER INFORMATION: primer, ClKASIV/Kmr-R

<400> SEQUENCE: 51
ttcgctgggt ttatcctaat tgtaaggggc gaagagtata g            41
```

METHOD OF PRODUCING LIPID

TECHNICAL FIELD

The present invention relates to a method of producing a lipid and a transformant using the same.

BACKGROUND ART

Fatty acids are one of the principal components of lipids. In vivo, fatty acids are bonded to glycerin via an ester bond to form lipids such as triacylglycerol. Further, many animals and plants also store and utilize fatty acids as an energy source. These fatty acids and lipids (fats and oils) stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkylbenzenesulfonic acid salts and the like are utilized as anionic surfactants. Further, polyoxyalkylene alkyl ethers, alkyl polyglycosides and the like are utilized as nonionic surfactants. These surfactants are used for detergents or disinfectants. Cationic surfactants such as alkylamine salts and mono- or dialkyl-quaternary ammonium salts, as other higher alcohol derivatives, are commonly used for fiber treatment agents, hair conditioning agents or disinfectants. Further, benzalkonium type quaternary ammonium salts are commonly used for disinfectants or antiseptics. Furthermore, vegetable fats and oils are used also as raw materials of biodiesel fuels.

A fatty acid synthesis pathway of plants is localized in a chloroplast. In the chloroplast, an elongation reaction of the carbon chain is repeated starting from an acetyl-ACP (acyl-carrier-protein), and finally an acyl-ACP (a composite consisting of an acyl group being a fatty acid residue and an acyl-carrier-protein) having 16 or 18 carbon atoms is synthesized. A β-ketoacyl-ACP synthase (β-ketoacyl-acyl-carrier-protein synthase: hereinafter, also referred to as "KAS") is an enzyme involved in control of chain length of the acyl group, among enzymes involved in the fatty acid synthesis pathway. In the plants, four kinds of KASs having different function respectively, namely KAS I, KAS II, KAS III and KAS IV are known to exist. Among these, KAS III functions in a stage of starting a chain length elongation reaction to elongate the acetyl-ACP having 2 carbon atoms to the acyl-ACP having 4 carbon atoms. In the subsequent elongation reaction, KAS I, KAS II and KAS IV are involved. KAS I is mainly involved in the elongation reaction to the palmitoyl-ACP having 16 carbon atoms, and KAS II is mainly involved in the elongation reaction to the stearoyl ACP having 18 carbon atoms. On the other hand, it is believed that KAS IV is involved in the elongation reaction to medium chain acyl-ACP having 6 to 14 carbon atoms. Less knowledge for the KAS IV is obtained even in the plants, the KAS IV is considered to be KAS characteristic to the plants accumulating a medium chain fatty acid, such as *Cuphea* (see Patent Literature 1 and Non-Patent Literature 1).

Cyanobacteria (blue-green bacteria) belong to a group of eubacteria, and have an ability to produce oxygen through photosynthesis and fix carbon dioxide. Cyanobacteria, which have an outer membrane and a cell wall formed of peptidoglycan, and fall into the category of gram-negative bacteria. However, cyanobacteria are phylogenetically far from typical gram-negative bacteria in the taxonomy. More than billion years ago, cyanobacteria were engulfed by eukaryotic cells. Such intracellular symbiont (primary symbiosis), cyanobacteria, are considered as an origin of chloroplasts. Thus cyanobacteria have been widely used in photosynthesis studies as an ancestor organism of chloroplasts. Further, cyanobacteria grow faster than other plants, and have high photosynthetic ability. Furthermore, cyanobacteria also have a transformation ability.

Because of this, cyanobacteria, to which foreign DNA is introduced in the cells, can be used in microbiological production of substances, and thus have attracted attention as a host for producing substances such as biofuel.

As examples of producing substances using cyanobacteria, production of fatty acids has been reported (Non-Patent Literature 2). However, with regard to a technology on the production of fatty acids, depending on the photosynthesis of cyanobacteria and using carbon dioxide in the atmosphere or the like as a carbon source, productivity thereof has still remained at a low level.

CITATION LIST

Patent Literatures

Patent Literature 1: WO 98/46776

Non-Patent Literatures

Non-Patent Literature 1: Dehesh K. et al The Plant Journal, 1998, vol. 15(3), p. 383-390
Non-Patent Literature 2: Liu X. et al., Proc. Natl. Acad. Sci. USA, 2011, vol. 108, p. 6899-6904

SUMMARY OF INVENTION

The present invention relates to a method of producing a lipid, containing the steps of:
culturing a transformant obtained by introducing a gene encoding the following protein (a) or (b) into cyanobacteria, and
producing fatty acids or a lipid containing the fatty acids as components:
(a) a protein consisting of the amino acid sequence set forth in SEQ ID NO: 1; and
(b) a protein consisting of an amino acid sequence having 60% or more identity with the amino acid sequence of the protein (a), and having β-ketoacyl-ACP synthase activity (hereinafter, also referred to as "KAS activity").

Further, the present invention relates to a transformant obtained by introducing a gene encoding the protein (a) or (b) into cyanobacteria.

MODE FOR CARRYING OUT THE INVENTION

The present invention relates to a method of producing a lipid using cyanobacteria, containing enhancing productivity of medium chain fatty acids or the lipid containing these fatty acids as components and the total amount of fatty acids to be produced.

Further, the present invention relates to a transformant of cyanobacteria in which the productivity of medium chain fatty acids or the lipid containing these fatty acids as components and the productivity of total fatty acids to be produced are enhanced.

The present inventors focused on KAS of algae of genus *Nannochloropsis* being one kind of algae as KAS to be introduced into a host in order to improve productivity of medium chain fatty acids and a total amount of fatty acids to be produced. Then, when the transformant was prepared by introducing a gene encoding the KAS of the algae of the genus *Nannochloropsis* into cyanobacteria, the present inventors found that the productivity of medium chain fatty acids to be produced by the transformant or the lipid containing these fatty acids as components, and the total amount of fatty acids to be produced are significantly improved.

The present invention was completed based on these findings.

According to the method of producing the lipid of the present invention, the productivity of medium chain fatty acids or the lipid containing these fatty acids as components, and the total amount of fatty acids to be produced can be improved.

Moreover, the transformant of the present invention is excellent in the productivity of medium chain fatty acids or the lipid containing these fatty acids as components, and the productivity of total fatty acids to be produced.

Other and further features and advantages of the invention will appear more fully from the following description.

The term "lipid(s)" in the present specification, covers simple lipids such as neutral lipids, wax, and ceramides; complex lipids such as phospholipids, glycolipids, and sulfolipids; and derived lipids obtained from these lipids such as fatty acids, alcohols, and hydrocarbons.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell., Cold Spring Harbor Laboratory Press], and examples thereof include conditions where hybridization is performed by incubating a solution containing 6×SSC (composition of 1×SSC: 0.15M sodium chloride, 0.015M sodium citrate, pH7.0), 0.5% SDS, 5×Denhardt and 100 mg/mL herring sperm DNA together with a probe at 65° C. for 8 to 16 hours.

A transfromant of the present invention is transformed by a gene encoding the following protein (a) or (b) (hereinafter, also referred to as "KAS gene").

(a) A protein consisting of the amino acid sequence set forth in SEQ ID NO: 1.
(b) A protein consisting of an amino acid sequence having 60% or more identity with the amino acid sequence of the protein (a), and having KAS activity (a protein functionally equivalent to the protein (a)).

The protein consisting of the amino acid sequence set forth in SEQ ID NO: 1 is a KAS derived from *Nannochloropsis oculata* NIES2145 being algae of the genus *Nannochloropsis*.

The KAS is an enzyme involved in control of chain length of an acyl group in the fatty acid synthesis pathway. The fatty acid synthesis pathway of algae is also localized in the chloroplast in a similar manner to that of plants. In the chloroplast, the elongation reaction of the carbon chain is repeated starting from the acetyl-ACP, and finally an acyl-ACP having 16 or 18 carbon atoms is synthesized. Then, an acyl-ACP thioesterase (hereinafter, also referred to as "TE") hydrolyzes the thioester bond of the acyl-ACP to form free fatty acids.

In the first stage of the fatty acid synthesis, an acetoacetyl-ACP is formed by a condensation reaction between the acetyl-ACP and a malonyl-ACP. The KAS catalyzes the reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

In the present specification, an expression "KAS activity" means the activity to catalyze the condensation reaction of the acetyl-ACP or the acyl-ACP with the malonyl-ACP.

The KAS activity of the protein can be confirmed by, for example, introducing a fusion gene produced by linking a gene encoding the prtein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a fusion gene produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses acyl-ACPs, as substrates.

KAS is categorized into KAS I, KAS II, KAS III and KAS IV according to substrate specificity. KAS III uses an acetyl-ACP having 2 carbon atoms as the substrate to catalyze the elongation reaction that the acetyl-ACP having 2 carbon atoms is converted to the acyl-ACP having 4 carbon atoms. KAS I mainly catalyzes the elongation reaction that the acyl-ACP having 4 carbon atoms is converted to the acyl-ACP having 16 carbon atoms, to synthesize the palmitoyl-ACP having 16 carbon atoms. KAS II mainly catalyzes the elongation reaction that the acyl-ACP having 16 carbon atoms is converted to the acyl-ACP having 18 carbon atoms, to synthesize the stearoyl-ACP having 18 carbon atoms. KAS IV catalyzes the elongation reaction that the acyl-ACP having 6 carbon atoms is converted to the acyl-ACP having 14 carbon atoms, to synthesize a medium chain acyl-ACP.

As shown in Examples mentioned later, the protein (a) has substrate specificity to the medium chain acyl-ACP. Therefore, the protein (a) is considered to be KAS IV. Herein, the term "substrate specificity to medium chain acyl-ACP" means that the KAS mainly uses an acyl-ACP having 4 to 12 carbon atoms as the substrate and catalyzes the elongation reaction for the synthesis of the medium chain acyl-ACP having up to 14 carbon atoms. Moreover, in the present specification, the term "medium chain" means that the number of carbon atoms of the acyl group is 6 or more and 14 or less.

The substrate specificity of the KAS to the medium chain acyl-ACP can be confirmed by, for example, introducing a fusion gene produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or the cultured liquid by an ordinary technique. Alternatively, the substrate specificity to the medium chain acyl-ACP can be confirmed by allowing, in the above-described system, coexpression of TE having substrate specificity to the medium chain acyl-ACP mentioned later, and being compared with fatty acid composition in the case of allowing single expression of TE having substrate specificity to the medium chain acyl-ACP. Alternatively, the specificity to the medium chain acyl-ACP can be confirmed by introducing a fusion gene produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses medium chain acyl-ACPs, as substrates.

In the protein (b), the identity with the amino acid sequence of the protein (a) is preferably 70% or more, more preferably 80% or more, further preferably 90% or more, furthermore preferably 91% or more, and furthermore preferably 95% or more, in view of KAS activity.

Specific examples of the protein (b) include the following protein (a1).

(a1) A protein consisting of the amino acid sequence set forth in SEQ ID NO: 3.

The protein consisting of the amino acid sequence set forth in SEQ ID NO: 3 is a KAS derived from *Nannochloropsis gaditana* CCMP526. The amino acid sequence set forth in SEQ ID NO: 3 has about 90% identity with the amino acid sequence set forth in SEQ ID NO: 1.

Further, specific examples of the protein (b) include a protein in which 1 or several (for example 1 or more and 184 or less, preferably 1 or more and 138 or less, more preferably 1 or more and 92 or less, further preferably 1 or more and 46 or less, furthermore preferably 1 or more and 42 or less, and furthermore preferably 1 or more and 23 or less) amino acids are deleted, substituted, inserted or added to the amino acid sequence of the protein (a) or (a1). A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the Splicing overlap extension (SOE)-PCR reaction, the ODA method, and the Kunkel method. Further, commercially available kits such as Site-Directed Mutagenesis System Mutan-SuperExpress Km kit (trade name, manufactured by Takara Bio), Transformer™ Site-Directed Mutagenesis kit (trade name, manufactured by Clonetech Laboratories), and KOD-Plus-Mutagenesis Kit (trade name, manufactured by Toyobo) can also be utilized. Furthermore, a gene containing a desired mutation can also be obtained by introducing a genetic mutation at random, and then performing an evaluation of the enzyme activities and a gene analysis thereof by an appropriate method.

An example of the KAS gene includes a gene consisting of the following DNA (d) or (e).

(d) A DNA consisting of the nucleotide sequence set forth in SEQ ID NO: 2.
(e) A DNA consisting of a nucleotide sequence having 60% or more identity with the nucleotide sequence of the DNA (d), and encoding a protein having KAS activity.

The nucleotide sequence set forth in SEQ ID NO: 2 is a nucleotide sequence of a gene encoding a protein consisting of the amino acid sequence set forth in SEQ ID NO: 1.

In the DNA (e), from the point of view of KAS activity, the identity with the nucleotide sequence of the DNA (d) is preferably 65% or more, more preferably 70% or more, further preferably 75% or more, furthermore preferably 78% or more, furthermore preferably 80% or more, furthermore preferably 90% or more, and furthermore preferably 95% or more.

Further, the DNA (e) is also preferably a DNA in which 1 or several (for example 1 or more and 546 or less, preferably 1 or more and 478 or less, more preferably 1 or more and 410 or less, further preferably 1 or more and 342 or less, furthermore preferably 1 or more and 301 or less, furthermore preferably 1 or more and 273 or less, furthermore preferably 1 or more and 137 or less, and furthermore preferably 1 or more and 69 or less) nucleotides are deleted, substituted, inserted or added to the nucleotide sequence set forth in SEQ ID NO: 2, and encoding a protein having KAS activity.

Furthermore, the DNA (e) is also preferably a DNA capable of hybridizing with a DNA consisting of a nucleotide sequence complementary with the DNA (d) under a stringent condition, and encoding the protein (a) or (b) having KAS activity.

Specific examples of the DNA (e) include the following DNA (d1).

(d1) A DNA consisting of the nucleotide sequence set forth in SEQ ID NO: 4.

The nucleotide sequence set forth in SEQ ID NO: 4 is a nucleotide sequence of a gene encoding a protein consisting of the amino acid sequence set forth in SEQ ID NO: 3. The nucleotide sequence set forth in SEQ ID NO: 4 has about 77% identity with the nucleotide sequence set forth in SEQ ID NO: 2.

The KAS gene can be obtained by genetic engineering techniques that are ordinarily carried out. For example, the KAS gene can be artificially synthesized based on the amino acid sequence set forth in SEQ ID NO: 1 or the nucleotide sequence set forth in SEQ ID NO: 2. The synthesis of the KAS gene can be achieved by utilizing, for example, the services of Invitrogen. Further, the gene can also be obtained by cloning from the genome of *Nannochloropsis oculata*. The cloning can be carried out by, for example, the methods described in Molecular Cloning—A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant of the present invention preferably has a gene encoding TE (hereinafter, also referred to as "TE gene"), in addition to the KAS gene, introduced into a host.

TE is an enzyme that hydrolyzes the thioester bond of the acyl-ACP synthesized by a fatty acid synthetase such as the KAS to produce free fatty acids. The function of the TE terminates the fatty acid synthesis on the ACP, and then the thus-hydrolyzed fatty acids are supplied to the synthesis of triglyceride and the like. Therefore, lipid productivity of the transformant, particularly, productivity of fatty acids can be further improved by introducing the KAS gene and the TE gene into the host.

The TE that can be used in the present invention only needs to be the protein having acyl-ACP thioesterase activity (hereinafter, also referred to as "TE activity"). Herein, the "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, they are considered to be an important factor in determining the fatty acid composition of an organism.

As described above, the protein (a) or (b) is a KAS having substrate specificity to the medium chain acyl-ACP. Therefore, TEs to be introduced are also preferably genes encoding TE having substrate specificity to the medium chain acyl-ACP. The productivity of medium chain fatty acids can be further improved by using TE having substrate specificity to the medium chain acyl-ACP. In particular, when a host originally having no genes encoding TE having substrate specificity to the medium chain acyl-ACP is used in the transformation, introduction of genes encoding TE having substrate specificity to the medium chain acyl-ACP is effective.

The TE that can be used in the present invention can be appropriately selected from ordinary TEs and proteins functionally equivalent to the TEs, according to a kind of host or the like.

Specific examples thereof include TE of *Cuphea calophylla* subsp. *mesostemon* (GenBank ABB71581); TE of *Cinnamomum camphora* (GenBank AAC49151.1); TE of *Myristica fragrans* (GenBank AAB71729 and AAB71730); TE of *Cuphea lanceolata* (GenBank CAA54060); TE of *Cuphea hookeriana* (GenBank Q39513); TE of *Ulumus americana* (GenBank AAB71731); TE of *Sorghum bicolor* (GenBank EER87824); TE of *Sorghum bicolor* (GenBank EER88593); TE of *Cocos nucifera* (CnFatB1: see Jing et al. BMC Biochemistry 2011, 12:44); TE of *Cocos nucifera* (CnFatB2: see Jing et al. BMC Biochemistry 2011, 12:44); TE of *Cuphea viscosissima* (CvFatB1: see Jing et al. BMC Biochemistry 2011, 12:44); TE of *Cuphea viscosissima* (CvFatB2: see Jing et al. BMC Biochemistry 2011, 12:44); TE of *Cuphea viscosissima* (CvFatB3: see Jing et al. BMC Biochemistry 2011, 12:44); TE of *Elaeis guineensis* (GenBank AAD42220); TE of *Desulfovibrio vulgaris* (GenBank ACL08376); TE of *Bacteriodes fragilis* (GenBank CAH09236); TE of *Parabacteriodes distasonis* (GenBank ABR43801); TE of *Bacteroides thetaiotaomicron* (GenBank AA077182); TE of *Clostridium asparagiforme* (GenBank EEG55387); TE of *Bryanthella formatexiqens* (GenBank EET61113); TE of *Geobacillus* sp. (GenBank EDV77528); TE of *Streptococcus dysgalactiae* (GenBank BAH81730); TE of *Lactobacillus brevis* (GenBank ABJ63754); TE of *Lactobacillus plantarum* (GenBank CAD63310); TE of *Anaerococcus tetradius* (GenBank EEI82564); TE of *Bdellovibrio bacteriovorus* (GenBank CAE80300); TE of *Clostridium thermocellum* (GenBank ABN54268); TE of *Arabidopsis thaliana*; TE of *Bradyrhizobium japonicum*; TE of *Brassica napus*; TE of *Cinnamonum camphorum*; TE of *Capsicum chinense*; TE of *Cuphea hookeriana*; TE of *Cuphea lanceolata*; TE of *Cuphea palustris*; TE of *Coriandrum sativum* L.; TE of *Carthamus tinctorius*; TE of *Cuphea wriqhtii*; TE of *Gossypium hirsutum*; TE of *Garcinia manqostana*; TE of *Helianthus annuus*; TE of *Iris germanica*; TE of *Iris tectorum*; TE of *Triticum aestivum*; TE of *Ulmus Americana*; TE of *Escherichia coli*; TE of *Cocos nucifera* (CnFatB3: see Jing et al. BMC Biochemistry 2011, 12:44, SEQ ID NO: 5, the nucleotide sequence of the gene encoding this TE: SEQ ID NO: 6); TE of *Nannochloropsis oculata* (SEQ ID NO: 7, the nucleotide sequence of the gene encoding this TE: SEQ ID NO: 8); TE of *Umbellularia californica* (GenBank AAA34215.1, SEQ ID NO: 9, the nucleotide sequence of the gene encoding this TE: SEQ ID NO: 10); TE of *Nannochloropsis gaditana* (SEQ ID NO: 11, the nucleotide sequence of the gene encoding this TE: SEQ ID NO: 12); TE of *Nannochloropsis qranulata* (SEQ ID NO: 13, the nucleotide sequence of the gene encoding this TE: SEQ ID NO: 14); and TE of *Symbiodinium microadriaticum* (SEQ ID NO: 15, the nucleotide sequence of the gene encoding this TE: SEQ ID NO: 16). Moreover, as the proteins functionally equivalent to the TEs, a protein consisting of an amino acid sequence having 50% or more (preferably 70% or more, more preferably 80% or more, or further preferably 90% or more) identity with the amino acid sequence of any one of the above-described TEs, and having TE activity, can be also used. Furthermore, a protein in which 1 or several (for example 1 or more and 147 or less, preferably 1 or more and 119 or less, more preferably 1 or more and 59 or less, or further preferably 1 or more and 30 or less) amino acids are deleted, substituted, inserted or added to the amino acid sequence of any one of the above-described TEs, and having TE activity, can be also used.

Among the TEs, TE having substrate specificity to the medium chain acyl-ACP is preferable. In particular, TE of *Umbellularia californica*, TE of *Cocos nucifera*, TE of *Cinnamonum camphorum*, TE of *Nannochloropsis oculata*, TE of *Nannochloropsis qaditana*, TE of *Nannochloropsis qranulata*, and TE of *Symbiodinium microadriaticum*; and a protein consisting of an amino acid sequence having 50% or more (preferably 70% or more, more preferably 80% or more, or further preferably 90% or more) identity with the amino acid sequence of any one of these TEs, and having TE activity designating substrate specificity to the medium chain acyl-ACP; and a protein in which 1 or several (for example 1 or more and 147 or less, preferably 1 or more and 119 or less, more preferably 1 or more and 59 or less, or further preferably 1 or more and 30 or less) amino acids are deleted, substituted, inserted or added to the amino acid sequence of these TEs, and having TE activity designating substrate specificity to the medium chain acyl-ACP; are more preferable.

The amino acid sequence information of these TEs, the nucleotide sequence information of the genes encoding them, and the like can be obtained from, for example, National Center for Biotechnology Information (NCBI).

TE has specificity to a chain length and a degree of unsaturation of fatty acids of acyl-ACP serving as the substrate. Accordingly, a kind of TE to be introduced is changed to allow cyanobacteria to produce free fatty acids having a desired chain length and a desired degree of unsaturation.

For example, TE derived from *Umbellularia californica* (UcTE) has substrate specificity to an acyl group having 12 carbon atoms, and the free fatty acids to be produced are mainly free fatty acids having 12 carbon atoms such as lauric acid (C12:0). Further, TEs of *Cinnamonum camphorum* and *Cocos nucifera* have substrate specificity to an acyl group having 14 carbon atoms, and the free fatty acids to be produced are mainly free fatty acids having 14 carbon atoms such as myristic acid (C14:0). Furthermore, TE of *Escherichia coli* K-12 strains has substrate specificity to an acyl group having 16 or 18 carbon atoms, and the free fatty acids to be produced are mainly free fatty acids having 16 or 18 carbon atoms such as palmitic acid (C16:0), palmitoleic acid (C16:1), stearic acid (C18:0), oleic acid (C18:1), linoleic acid (C18:2) and linolenic acid (C18:3).

In the present invention, the TE activity can be confirmed by, for example, introducing a fusion gene produced by linking the TE gene to the downstream of a promoter which functions in a host cell, into a host cell which lacks a fatty acid degradation system, culturing the thus-obtained cell under the conditions suitable for the expression of the introduced TE gene, and analyzing any change caused thereby in the fatty acid composition of the host cell or the cultured liquid by an ordinary technique. Alternatively, the TE activity can be confirmed by introducing a fusion gene produced by linking the TE gene to the downstream of a promoter which functions in a host cell, into a host cell, culturing the thus-obtained cell under the conditions suitable for the expression of the introduced TE gene, and subjecting a disruption liquid of the cell to a reaction which uses acyl-ACPs, as substrates, prepared according to the method of Yuan et al. (Yuan L. et al., Proc. Natl. Acad. Sci. USA, 1995, vol. 92(23), p. 10639-10643).

The transformant of the present invention can be obtained by introducing the KAS gene, into cyanobacteria described later. In the transformant, in comparison with the host itself, the ability to produce the medium chain fatty acids, and the lipid containing the fatty acids as components is significantly improved, and the total amount of the fatty acids to be produced is also significantly improved. The ability to produce fatty acids and a lipid of the host and the transformant can be measured by the method used in Examples described below.

Cyanobacteria used as the host of the transformant of the present invention are one group of procaryotes that perform photosynthesis using chlorophyll.

Cyanobacteria are highly diversified. In view of cell morphology, there are bacteria having a unicellular shape such as *Synechocystis* sp. PCC6803, bacteria having a filamentous shape formed of many cells connected like a string such as *Anabaena* sp. PCC7120 forming heterocysts and fixing nitrogen, and bacteria having a spiral shape and a branched shape.

In view of growth environment, there are species adapted in various conditions including thermophilic bacteria such as *Thermosynechococcus elonqatus* BP-1 isolated from Beppu Onsen; and oceanic bacteria such as *Synechococcus* sp. CC9311 living in the coast or *Synechococcus* sp. WH8102 living in the outer sea.

As bacteria having feature intrinsic to the species, *Microcystis aeruginosa*, which has gas vacuoles and can produce toxin; *Gloeobacter violaceus* PCC7421 having no thylakoid and a light harvesting antenna, i.e., phycobilisome, bound to plasma membrane; and oceanic *Acaryochloris marina* having chlorophyll d as a main (>95%) photosynthetic pigment in place of chlorophyll a, as is in general photosynthetic organisms, are also mentioned.

In cyanobacteria, carbon dioxide fixed by photosynthesis is converted into acetyl-CoA via a large number of enzymatic reaction processes. In the initial stage of fatty acid synthesys, malonyl-CoA is synthesized from acetyl-CoA and $CO_2$ by the function of acetyl-CoA carboxylase. Next, malonyl-CoA is converted into malonyl-ACP by the function of malonyl-CoA:ACP transacylase. Thereafter, while fatty acid synthetase (or acyl-ACP synthetase) progressively works, two carbon units are sequentially added to synthesize acyl-ACP, which are increased in two carbons and used as an intermediate for synthesizing e.g., a membrane lipid.

Every kind of cyanobacteria can be used as the host of the transformant of the present invention. Specific examples of the cyanobacteria include cyanobacteria of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*. Among these, cyanobacteria of the genus *Synechocystis*, the genus *Synechococcus*, the genus *Thermosynechococcus*, or the genus *Anabaena* are preferable, and cyanobacteria of the genus *Synechocystis* or the genus *Synechococcus* are more preferable. Further, the host used in the present invention is preferably *Synechocystis* sp. PCC6803, *Synechocystis* sp. PCC7509, *Synechocystis* sp. PCC6714, *Synechococcus elongatus* sp. PCC7942, *Thermosynechococcus elongatus* BP-1, *Trichodesmium erythraeum* IMS101, *Acaryochloris mariana* MBIC11017, *Crocosphaera watsonii* WH8501, or *Anabaena* sp. PCC7120, more preferably *Synechocystis* sp. PCC6803 or *Synechococcus elongatus* sp. PCC7942, and further preferably *Synechococcus elongatus* sp. PCC7942.

The transformant of the present invention can be obtained by introducing the KAS gene into the host according to an ordinary technique. Specifically, the transformant of the present invention can be produced by preparing an expression vector capable of expressing the KAS gene in a host cell, and introducing it into a host cell to transform the host cell.

In addition to the KAS gene, a transformant, to which the TE gene is introduced, can also be also produced according to an ordinary technique.

A vector for use as the plasmid vector for gene expression (plasmid) may be any vector capable of introducing the gene encoding the objective protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the expression vector that can be preferably used in the present invention include a pUC-based vector (manufactured by Takara Bio), pBluescript (pBS) II SK(−) (manufactured by Stratagene), a pSTV-based vector (manufactured by Takara Bio), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (Mckenzie, T. et al., (1986), Plasmid 15(2); p. 93-103), pBR322 (manufactured by Takara Bio), pRS403 (manufactured by Stratagene), pMW218/219 (manufactured by Nippon Gene), a pRI-based vector (manufactured by Takara Bio), a pBI-based vector (manufactured by Clontech), and an IN3-based vector (manufactured by Inplanta Innovations). Among these, a pUC-based vector is more preferable.

Moreover, a kind of promoter regulating the expression of the gene encoding an objective protein introduced into the expression vector can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a derivative that can be derived by addition of isopropyl β-D-1-thiogalactopyranoside (IPTG), Rubisco operon (rbc), PSI reaction center protein (psaAB), D1 protein of PSII (psbA), and a promoter of a rrnA operon gene encoding ribosomal RNA. Among these, a promoter of a rrnA operon gene is more preferable.

Moreover, a kind of selection marker for confirming introduction of the gene encoding an objective protein can also be appropriately selected according to a kind of the host to be used. Examples of the selection marker that can be preferably used in the present invention include drug resistance genes such as a chloramphenicol resistance gene, an erythromycin resistance gene, a neomycin resistance gene, a kanamycin resistance gene, a spectinomycin resistance gene, and a gentamicin resistance gene. Further, it is also possible to use a deletion of an auxotrophy-related gene or the like as the selection marker gene.

Introduction of the gene encoding an objective protein to the vector can be conducted by an ordinary technique such as restriction enzyme treatment and ligation.

Further, the heterogeneous gene to be introduced into cyanobacteria is preferably optimized in codon in accordance with use frequency of codon in the cyanobacteria. Information of codons used in each of organisms is available from Codon Usage Database (www.kazusa.or.jp/codon/).

Furthermore, the method for transformation can be appropriately selected from ordinary techniques according to a kind of the host to be used. Specific examples of the method for transformation include a spontaneous transformation method, an electroporation method, and a jointing method.

The host used in the transformant of the present invention is preferably cyanobacteria in which a function of acyl-ACP synthetase (hereinafter, also referred to as "aas") is lost. An ability to secrete the lipid produced by the transformant can be improved by using, as the host, cyanobacteria in which the function of aas is lost.

Herein, "aas" means one kind of enzyme related to fatty acid synthesis, and has a function of forming a thioester bond in an ATP-dependent manner by using the free fatty acids and an ACP protein as the substrate to produce acyl-ACP. Accumulation and secretion of fatty acids are known to be promoted by causing loss of the function of aas in cyanobacteria (see Plant Physiology, 2010, vol. 152(3), pp. 1598-1610).

In the present specification, an expression "causing loss of the function of aas" means causing loss of an acyl-ACP synthesis function of aas of the host.

Method for causing loss of the function of aas can be appropriately selected from the methods for causing loss of the function of a protein that are ordinarily used. Examples of the methods include methods deleting or inactivating a gene encoding aas (hereinafter, also referred to as "aas gene"), methods of introducing the mutation that inhibits transcription of aas gene, methods of inhibiting translation of a transcript of aas gene, and methods of administering an inhibitor specifically inhibiting aas. Examples of the means for deleting or inactivating the aas gene include introduction of a mutation of one or more nucleotides in the nucleotide sequence of the aas gene, substitution or insertion of a different nucleotide sequence in the nucleotide sequence of the aas gene, and deletion of a part or a whole nucleotide sequence of the aas gene. Examples of the means for introducing a mutation which inhibits transcripton of the aas gene include introduction of a mutation in a promoter resion of the aas gene and deletion or inactivation of the promoter by substitution or insertion of a different nucleotide sequence. Examples of a specific method for introducing the mutation and for substituting or inserting a nucleotide sequence include ultraviolet irradiation and site-specific mutagenesis, homologous recombination method and SOE (splicing by overlap extension)-PCR method. Examples of the means of for inhibiting the translation of a transcript include interference of RNA by micro RNA. Examples of an aas-specific inhibitor include aas and a specific antibody against its receptor or ligand.

In the present invention, a method for deleting or inactivating the aas gene of cyanobacteria is preferable in order to cause loss of the function of aas in cyanobacteria. In addition, information on an amino acid sequence of aas, a position of the aas gene and the nucleotide sequence thereof in cyanobacteria can be acquired from CyanoBase (genome.microbedb.jp/cyanobase/) and NCBI database ([www.ncbi.nlm.nih.gov/genome/] or [www.ncbi.nlm.nih.gov/protein/]).

As the aas, SIr1609 of *Synechocystis* sp. PCC6803, Syn7509DRAFT_00010940 of *Synechocystis* sp. PCC7509, Synpcc7942_0918 of *Synechococcus elongatus* sp. PCC7942, TI11301 of *Thermosynechococcus elongatus* BP-1, Tery_1829 of *Trichodesmium erythraeum* IMS101, AM1_5562 and AM1_2147 of *Acaryochloris mariana* MBIC11017, Cwat_5663 of *Crocosphaera watsonii* WH8501, Alr3602 of *Anabaena* sp. PCC7120 and the like are known.

Moreover, as the aas gene, a SIr1609 gene of *Synechocystis* sp. PCC6803 (NCBI Gene ID: 953643), a Syn7509DRAFT_00010940 gene of *Synechocystis* sp. PCC7509 (GenBank ID: ELR87398.1), a Synpcc7942_0918 gene of *Synechococcus elongatus* sp. PCC7942 (SEQ ID NO: 46), a TI11301 gene of *Thermosynechococcus elongatus* BP-1, a Tery_1829 gene of *Trichodesmium erythraeum* IMS101, an AM1_5562 gene and an AM1_2147 gene of *Acaryochloris mariana* MBIC11017, a Cwat_5663 gene of *Crocosphaera watsonii* WH8501, an Alr3602 gene of *Anabaena* sp. PCC7120 and the like are known. The "aas gene" in the present specification include the genes; a gene in which the identity with the nucleotide sequence of these genes is 40% or more, preferably 50% or more, more preferably 60% or more, further preferably 70% or more, furthermore preferably 80% or more, and furthermore preferably 90% or more, and encoding a polypeptide having an ability of synthesizing the acyl-ACP; and a gene in which 1 or several nucleotides, ordinarily 1 or more and 1,170 or less nucleotides, preferably 1 or more and 975 or less nucleotides, more preferably 1 or more and 780 or less nucleotides, further preferably 1 or more and 585 or less nucleotides, furthermore preferably 1 or more and 390 or less nucleotides, and further preferably 1 or more and 195 or less nucleotides, are deleted, substituted, inserted or added to the nucleotide sequence of these genes, and encoding a polypeptide having an ability of synthesizing the acyl-ACP.

In order to cause loss of the function of aas in cyanobacteria, a heterologous gene, preferably the above-mentioned TE gene is introduced into a coding region of the aas gene. The function of aas in cyanobacteria can be lost, and an ability to express TE can be provided by introducing the above-mentioned TE gene into the coding region of the aas gene. Moreover, the free fatty acids produced by the action of TE can be efficiently secreted by introducing the above-mentioned TE gene into the coding region of the aas gene.

As a method for causing loss of the function of aas in cyanobacteria, for example, a DNA fragment of the TE gene in which the DNA fragment in an aas gene region is added to both ends by an SOE-PCR method is constructed, and the resultant material is inserted into a vector. Then, the vector is introduced into cyanobacteria to cause homologous recombination with the aas gene region on a genome, and the TE gene is introduced into the aas gene region on the genome. Thus, the function of aas in cyanobacteria can be lost.

Alternatively, the TE gene may be introduced into a neutral site that does not influence cyanobacteria and on the genome of cyanobacteria even if the gene is introduced thereinto.

In the transformant of the present invention, productivity of the medium chain fatty acids or the lipid containing these fatty acids as components and productivity of the total fatty acids to be produced are improved in comparison with the host. Accordingly, if the transformant of the present invention is cultured under suitable conditions and then the lipid is collected from a cultured product obtained or growth product, the lipid can be efficiently produced. Herein, the "cultured product" means medium and a transformant subjected to cultivation, and the "growth product" means a transformant subjected to growth.

The transformant of the present invention can be cultured, according to liquid culture or a modified method thereof, by using a medium to be ordinarily used for culture of cyanobacteria, such as a BG-11 medium (J. Gen. Microbiol., 1979, vol. 111, p. 1-61), an A medium (Proc. Natl. Acad. Sci. U.S.A., 1980, vol. 77, p. 6052-6056) and an AA medium (Plant Physiol., 1955, vol. 30, p. 366-372).

The culture for producing lipid may be performed in a period during which bacterial cells are sufficiently grown to accumulate fatty acids in high concentrations, for example, from 7 to 45 days, preferably from 10 to 30 days, and more preferably from 14 to 21 days, by an aeration/spinner culture or shaking culture.

The method of collecting lipid produced in the transformant can be appropriately selected from ordinary techniques. For example, lipid components can be isolated and collected from the above-described cultured product, growth product or the transformant by means of filtration, centrifugation, cell disruption, gel filtration chromatography, ion exchange chromatography, chloroform/methanol extraction, hexane extraction, or ethanol extraction. In the case of cultivation of larger scales, lipid can be obtained by collecting oil components from the cultured product, growth product or the transformant through pressing or extraction, and then performing general purification processes such as degumming, deacidification, decoloration, dewaxing, and deodorization. After lipid components are isolated as such, the isolated lipid is hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

Moreover, when the transformant in which the function of aas is lost is used, produced lipid is secreted outside cells. Therefore, it is unnecessary to destroy bacterial cells in order to collect the lipid, and the cells remaining after collecting the lipid can be repeatedly used for production of the lipid.

The lipid obtained by the production method of the present invention preferably contains one or more selected from simple lipids and derived lipids, more preferably contains derived lipids, further preferably contains fatty acids or esters thereof, and furthermore preferably is fatty acids or esters thereof, in view of usability thereof. From usability for a surfactant or the like, the fatty acid or the ester thereof contained in the lipid is preferably a medium chain fatty acid or an ester thereof, more preferably a fatty acid having 12 to 14 carbon atoms or an ester thereof, further preferably a saturated fatty acid having 12 to 14 carbon atoms or an ester thereof, and furthermore preferably a lauric acid or a myristic acid or an ester thereof.

The lipid obtained by the production method of the present invention can be utilized for food, as well as an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing a lipid, transformants, methods of producing a transformant, and methods of enhancing productivity of a lipid.

<1> A method of producing a lipid, containing the steps of:
  culturing a transformant obtained by introducing a gene encoding the following protein (a) or (b) into cyanobacteria, and
  producing fatty acids or a lipid containing the fatty acids as components:
  (a) a protein consisting of the amino acid sequence set forth in SEQ ID NO: 1; and
  (b) a protein consisting of an amino acid sequence having 60% or more, preferably 70% or more, more preferably 80% or more, further preferably 90% or more, furthermore preferably 91% or more, and furthermore preferably 95% or more, identity with the amino acid sequence of the protein (a), and having KAS activity.

<2> The method described in the above item <1>, wherein the protein (b) is a protein (a1) consisting of the amino acid sequence set forth in SEQ ID NO: 3.

<3> The method described in the above item <1> or <2>, wherein the protein (b) is a protein in which 1 or several amino acids, for example 1 or more and 184 or less amino acids, preferably 1 or more and 138 or less amino acids, more preferably 1 or more and 92 or less amino acids, further preferably 1 or more and 46 or less amino acids, furthermore preferably 1 or more and 42 or less amino acids, and furthermore preferably 1 or more and 23 or less amino acids, are deleted, substituted, inserted or added to the amino acid sequence of the protein (a) or (a1).

<4> The method described in any one of the above items <1> to <3>, wherein the gene encoding the protein (a) or (b) is a gene consisting of the following DNA (d) or (e):
  (d) a DNA consisting of the nucleotide sequence set forth in SEQ ID NO: 2; and
  (e) a DNA consisting of a nucleotide sequence having 60% or more, preferably 65% or more, more preferably 70% or more, further preferably 75% or more, furthermore preferably 78% or more, furthermore preferably 80% or more, furthermore preferably 90% or more, and furthermore preferably 95% or more, identity with the nucleotide sequence of the DNA (d), and encoding a protein having KAS activity.

<5> The method described in the above item <4>, wherein the DNA (e) is a DNA consisting of a nucleotide sequence in which 1 or several nucleotides, preferably 1 or more and 546 or less nucleotides, more preferably 1 or more and 478 or less nucleotides, further preferably 1 or more and 410 or less nucleotides, furthermore preferably 1 or more and 342 or less nucleotides, furthermore preferably 1 or more and 301 or less nucleotides, furthermore preferably 1 or more and 273 or less nucleotides, furthermore preferably 1 or more and 137 or less nucleotides, and furthermore preferably 1 or more and 69 or less nucleotides, are deleted, substituted, inserted or added to the nucleotide sequence of the DNA (d), and encoding the protein (a) or (b) having KAS activity, or a DNA capable of hybridizing with a DNA consisting of a nucleotide sequence complementary with the DNA (d) under a stringent condition, and encoding the protein (a) or (b) having KAS activity.

<6> The method described in the above item <4> or <5>, wherein the DNA (e) is a DNA consisting of the nucleotide sequence set forth in SEQ ID NO: 4.

<7> The method described in any one of the above items <1> to <6>, wherein the lipid is a medium chain fatty acid or an ester thereof.

<8> The method described in any one of the above items <1> to <7>, wherein the protein (a) or (b) is a KAS having substrate specificity to a medium chain acyl-ACP.

<9> The method described in any one of the above items <1> to <8>, wherein a gene encoding TE having substrate specificity to a medium chain acyl-ACP is introduced to the cyanobacteria.

<10> The method described in the above item <9>, wherein the TE is at least one TE selected from the group consisting of TE of *Cocos nucifera*, TE of *Cinnamonum camphorum*, TE of *Nannochloropsis oculata*, TE of *Umbellularia californica*, TE of *Nannochloropsis gaditana*, TE of *Nannochloropsis granulate*, and TE of *Symbiodinium microadriaticum*.

<11> The method described in any one of the above items <1> to <10>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*, more preferably cyanobacteria of the genus *Synechococcus*.

<12> The method described in any one of the above items <1> to <11>, wherein a function of aas is lost in the cyanobacteria.

<13> The method described in the above item <12>, wherein an aas gene is deleted or inactivated in the cyanobacteria.

<14> The method described in the above item <13>, wherein the aas gene is selected from the group consisting of Slr1609 gene, Syn7509DRAFT_00010940 gene, Synpcc7942_0918 gene, Tll1301 gene, Tery_1829 gene, AM1_5562 gene, AM1_2147 gene, Cwat_5663 gene, Alr3602 gene, a gene in which the identity with the nucleotide sequence of these genes is 40% or more, preferably 50% or more, more preferably 60% or more, further preferably 70% or more, furthermore preferably 80% or more, and furthermore preferably 90% or more, and encoding a polypeptide having an ability of synthesizing an acyl-ACP, and a gene in which 1 or several nucleotides, ordinarily 1 or more and 1,170 or less nucleotides, preferably 1 or more and 975 or less nucleotides, more preferably 1 or more and 780 or less nucleotides, further preferably 1 or more and 585 or less nucleotides, furthermore preferably 1 or more and 390 or less nucleotides, and furthermore preferably 1 or more and 195 or less nucleotides, are deleted, substituted, inserted or added to the nucleotide sequence of these genes, and encoding a polypeptide having an ability of synthesizing the acyl-ACP, and preferably Slr1609 gene, Syn7509DRAFT_00010940 gene, Synpcc7942_0918 gene, Tll1301 gene, Tery_1829 gene, AM1_5562 gene, AM1_2147 gene, Cwat_5663 gene, or Alr3602 gene.

<15> The method described in any one of the above items <1> to <14>, culturing the transformant using BG-11 medium.

<16> The method described in any one of the above items <1> to <15>, wherein produced lipid is secreted outside cells of the transformant.

<17> The method described in any one of the above items <1> to <16>, enhancing productivity of lauric acid and myristic acid.

<18> A transformant obtained by introducing a gene encoding the protein (a) or (b) into cyanobacteria.

<19> A method of producing a transformant, introducing a gene encoding the protein (a) or (b) into cyanobacteria.

<20> A method of enhancing productivity of a lipid of cyanobacteria, introducing a gene encoding the protein (a) or (b) into cyanobacteria, and thereby enhancing productivity of the lipid of the obtained transformant.

<21> A method of modifying the composition of a lipid, containing the steps of:

introducing a gene encoding the protein (a) or (b) into cyanobacteria, and thereby obtaining a transformant, and enhancing productivity of medium chain fatty acids or a lipid containing the fatty acids as components produced in a cell of the transformant, to modify the composition of fatty acids or a lipid in all fatty acids or all lipids to be produced.

<22> The transformant or the method described in any one of the above items <18> to <21>, wherein the protein (b) is a protein (a1) consisting of the amino acid sequence set forth in SEQ ID NO: 3.

<23> The transformant or the method described in any one of the above items <18> to <22>, wherein the protein (b) is a protein in which 1 or several amino acids, for example 1 or more and 184 or less amino acids, preferably 1 or more and 138 or less amino acids, more preferably 1 or more and 92 or less amino acids, further preferably 1 or more and 46 or less amino acids, furthermore preferably 1 or more and 42 or less amino acids, and furthermore preferably 1 or more and 23 or less amino acids, are deleted, substituted, inserted or added to the amino acid sequence of the protein (a) or (a1).

<24> The transformant or the method described in any one of the above items <18> to <23>, wherein the gene encoding the protein (a) or (b) is a gene consisting of the DNA (d) or (e).

<25> The transformant or the method described in the above item <24>, wherein the DNA (e) is a DNA consisting of a nucleotide sequence in which 1 or several nucleotides, preferably 1 or more and 546 or less nucleotides, more preferably 1 or more and 478 or less nucleotides, further preferably 1 or more and 410 or less nucleotides, furthermore preferably 1 or more and 342 or less nucleotides, furthermore preferably 1 or more and 301 or less nucleotides, furthermore preferably 1 or more and 273 or less nucleotides, furthermore preferably 1 or more and 137 or less nucleotides, and furthermore preferably 1 or more and 69 or less nucleotides, are deleted, substituted, inserted or added to the nucleotide sequence of the DNA (d), and encoding the protein (a) or (b) having KAS activity, or a DNA capable of hybridizing with a DNA consisting of a nucleotide sequence complementary with the DNA (d) under a stringent condition, and encoding the protein (a) or (b) having KAS activity.

<26> The transformant or the method described in the above item <24> or <25>, wherein the DNA (e) is a DNA consisting of the nucleotide sequence set forth in SEQ ID NO: 4.

<27> The method described in any one of the above items <20> to <26>, wherein the lipid is a medium chain fatty acid or an ester thereof.

<28> The transformant or the method described in any one of the above items <18> to <29>, wherein the protein (a) or (b) is a KAS having substrate specificity to a medium chain acyl-ACP.

<29> The transformant or the method described in any one of the above items <18> to <28>, wherein a gene encoding TE having substrate specificity to a medium chain acyl-ACP is introduced to the cyanobacteria.

<30> The transformant or the method described in the above item <29>, wherein the TE is at least one TE selected from the group consisting of TE of *Cocos nucifera*, TE of *Cinnamonum camphorum*, TE of *Nannochloropsis oculata*, TE of *Umbellularia californica*, TE of *Nannochloropsis gaditana*, TE of *Nannochloropsis qranulata*, and TE of *Symbiodinium microadriaticum*.

<31> The transformant or the method described in any one of the above items <18> to <30>, wherein the cyanobacteria are cyanobacteria selected from the group consisting of the genus *Synechocystis*, the genus *Synechococcus*, the genus *Thermosynechococcus*, the genus *Trichodesmium*, the genus *Acaryochloris*, the genus *Crocosphaera*, and the genus *Anabaena*, preferably cyanobacteria of the genus *Synechocystis* or the genus *Synechococcus*, more preferably cyanobacteria of the genus *Synechococcus*.

<32> The transformant or the method described in any one of the above items <18> to <31>, wherein a function of aas is lost in the cyanobacteria.

<33> The transformant or the method described in the above item <32>, wherein the aas gene is deleted or inactivated in the cyanobacteria.

<34> The transformant or the method described in the above item <33>, wherein the aas gene is selected from the group consisting of SIr1609 gene, Syn7509DRAFT_00010940 gene, Synpcc7942_0918 gene, TII1301 gene, Tery_1829 gene, AM1_5562 gene, AM1_2147 gene, Cwat_5663 gene, Alr3602 gene, a gene in which the identity with the nucleotide sequence of these genes is 40% or more, preferably 50% or more, more preferably 60% or more, further preferably 70% or more, furthermore preferably 80% or more, and furthermore preferably 90% or more, and encoding a polypeptide having an ability of synthesizing an acyl-ACP, and a gene in which 1 or several nucleotides, ordinarily 1 or more and 1,170 or less nucleotides, preferably 1 or more and 975 or less nucleotides, more preferably 1 or more and 780 or less nucleotides, further preferably 1 or more and 585 or less nucleotides, furthermore preferably 1 or more and 390 or less nucleotides, and further preferably 1 or more and 195 or less nucleotides, are deleted, substituted, inserted or added to the nucleotide sequence of these genes, and encoding a polypeptide having an ability of synthesizing an acyl-ACP; and preferably SIr1609 gene, Syn7509DRAFT_00010940 gene, Synpcc7942_0918 gene, TII1301 gene, Tery_1829 gene, AM1_5562 gene, AM1_2147 gene, Cwat_5663 gene, or Alr3602 gene.

<35> The transformant or the method described in any one of the above items <18> to <34>, wherein produced lipid is secreted outside cells of the substrate transformant.

<36> The transformant or the method described in any one of the above items <18> to <35>, enhancing productivity of lauric acid and myristic acid.

EXAMPLES

Hereinafter, the present invention will be described more in detail with reference to Examples, but the present invention is not limited thereto.

Example Production of Lipid Utilizing KAS Derived from *Nannochloropsis oculata* Lipid was Produced Utilizing KAS Derived from *Nannochloropsis oculata*

Herein, the nucleotide sequences of the primers used in Examples and Comparative Examples described later are shown in Table 1.

TABLE 1

| SEQ ID NO: | Primer | Nucleotide sequence |
| --- | --- | --- |
| 24 | pUC118/0918up-F | 5'-GGATCCTCTAGAGTCAGCTCCGTTGTCGCAGTGTCAG-3' |
| 25 | 0918down/pUC118-R | 5'-GCATGCCTGCAGGTCAGACATCACTCAAGTCATCAGTC-3' |
| 26 | 0918up/spr-F | 5'-TCGGGCACCACAGGCATCGATTTTCGTTCGTG-3' |
| 27 | spr/0918down-R | 5'-AATCGGCTGGGGTTCCATATGCAAGGGTTTATTG-3' |
| 28 | 0918up-R | 5'-GCCTGTGGTGCCCGAGGTATAG-3' |
| 29 | 0918down-F | 5'-GAACCCCAGCCGATTGAAGATG-3' |
| 30 | Sp-F | 5'-ATCGATTTTCGTTCGTG-3' |
| 31 | 0918up/PpsbA1-F | 5'-TCGGGCACCACAGGCCTGGATTTAGCGTCTTCTAATCC-3' |
| 32 | PpsbA1/UcTE-R | 5'-AGAGGTGGTAGCCATATCGATCTTGAGGTTGTAAAGGG-3' |
| 33 | UcTE-F | 5'-ATGGCTACCACCTCTTTAGCTTC-3' |
| 34 | UcTE/spr-R | 5'-GAACGAAAATCGATTTACACGCGCGGTTCGGCGG-3' |
| 35 | pUC118/NS1up-F | 5'-GGATCCTCTAGAGTCAATGCCTTCTCCAAGGGCGGC-3' |
| 36 | NS1up/Kmr-R | 5'-TTCGCTGGGTTTATCCTTCTGGAGCAGGAAGATGTCG-3' |
| 37 | Kmr/NS1down-F | 5'-GGAATTTGTATCGATTCGAGTCCCTGCTCGTCACGC-3' |

TABLE 1-continued

| SEQ ID NO: | Primer | Nucleotide sequence |
|---|---|---|
| 38 | NS1down/pUC118-R | 5'-GCATGCCTGCAGGTCCGGCATGGCAATGTCTCTCTG-3' |
| 39 | Kmr-F | 5'-GATAAACCCAGCGAACCA-3' |
| 40 | Kmr-R | 5'-ATCGATACAAATTCCTCG-3' |
| 41 | NS1up-R | 5'-CTTCTGGAGCAGGAAGATGTCG-3' |
| 42 | 0918up/PrrnA-F | 5'-TCGGGCACCACAGGCAATTTGAGCGATCGAGAGGG-3' |
| 43 | PrrnA-R | 5'-AAGGGAAAACCTCCTTGGCTTAATTAATCTACCTAAC-3' |
| 44 | PrrnA/NoKASIV-F | 5'-AGGAGGTTTTCCCTTATGCGGGTCTCCAGTAGCGCCG-3' |
| 45 | NoKASIV/kmr-R | 5'-TTCGCTGGGTTTATCTTACTTGAACGGTTTGAAGATTAC-3' |
| 50 | PrrnA/CIKASIV-F | 5'-AGGAGGTTTTCCCTTATGGCGGCGGCCTCTTCCATGG-3' |
| 51 | CIKASIV/Kmr-R | 5'-TTCGCTGGGTTTATCCTAATTGTAAGGGGCGAAGAGTATAG-3' |

(1) Inactivation of aas Gene and Introduction of TE Gene in Cyanobacteria

From genomic DNA of wild-type strains of *Synechococcus elongatus* sp. PCC7942 strains, the primers pUC118/0918up-F (SEQ ID NO: 24) and 0918down/pUC118-R (SEQ ID NO: 25) described in Table 1 were used to amplify a fragment (2864 bp, SEQ ID NO: 47) containing a Synpcc7942_0918 gene (aas gene). The amplified fragment was inserted into a place between HincII sites of a pUC118 plasmid (Takara Bio) by applying an In-Fusion (registered trademark) PCR Cloning method (Clontech) to prepare pUC118-Synpcc7942_0918 plasmids into which the Synpcc7942_0918 gene (aas gene) was incorporated.

A pDG1726 plasmid (Guerout-Fleury et al., Gene, 1995, vol. 167, p. 335-336) was used as a template, and PCR was carried out by using the primers 0918up/spr-F (SEQ ID NO: 26) and spr/0918down-R (SEQ ID NO: 27) described in Table 1 to prepare spectinomycin resistance marker gene (SEQ ID NO: 17) fragments (hereinafter, also referred to as "sp fragment").

Next, the pUC118-Synpcc7942_0918 plasmid was used as a template, and PCR was carried out by using the primers 0918up-R (SEQ ID NO: 28) and 0918down-F (SEQ ID NO: 29) described in Table 1 to prepare linear DNA fragments in which a 927 bp region between coding regions of the Synpcc7942_0918 gene (aas gene) was deleted.

The linear DNA fragment and the sp fragment were bonded by applying the In-Fusion (registered trademark) PCR Cloning method (Clontech) to obtain pUC118-Synpcc7942_0918::sp plasmids containing a DNA sequence in the coding region of the Synpcc7942_0918 gene into which the sp fragment was inserted.

The pUC118-Synpcc7942_0918::sp plasmid was used as a template, and PCR was carried out by using the primers 0918up-R (SEQ ID NO: 28) and Sp-F (SEQ ID NO: 30) described in Table 1 to linearize the pUC118-Synpcc7942_0918::sp plasmid.

Further, PCR was carried out by using the primers 0918up/PpsbA1-F (SEQ ID NO: 31) and PpsbA1/UcTE-R (SEQ ID NO: 32) described in Table 1 to amplify a promoter region fragment (SEQ ID NO: 18) of a psbA1 gene derived from *Synechococcus elongatus* sp. PCC7942.

Furthermore, a sequence in which a codon was optimized in corresponding to *Synechocystis* sp. PCC6803 described in Liu X. et al., Proc. Natl. Acad. Sci. USA, 2011, vol. 108, pp. 6899-6904 was synthesized. The synthesized cDNA was used as a template, and PCR was carried out by using the primers UcTE-F (SEQ ID NO: 33) and UcTE/spr-R (SEQ ID NO: 34) described in Table 1 to amplify a fragment of a TE gene derived from *Umbellularia californica* (hereinafter, also referred to as "UcTE gene", SEQ ID NO: 19).

Then, the linearized pUC118-Synpcc7942_0918::sp plasmid, the promoter region fragment of the psbA1 gene and the fragment of the UcTE gene were mixed, and the resultant mixture was cloned by the In-Fusion (registered trademark) PCR Cloning method (Clontech) to obtain pUC118-Synpcc7942_0918::PpsbA1-UcTE-sp plasmids in which the promoter region fragment of the psbA1 gene, the fragment of the UcTE gene and the sp fragment were inserted into a place between the coding regions of the Synpcc7942_0918 gene in this order.

The wild-type strains of *Synechococcus elongatus* sp. PCC7942 were transformed by using the pUC118-Synpcc7942_0918::PpsbA1-UcTE-sp plasmid, by a spontaneous transformation method, and the resultant material was selected by spectinomycin resistance. Thus, the UcTE gene in which the codon was optimized was introduced into the place between the coding regions of the aas gene (Synpcc7942_0918 gene) on a genome to prepare A0918::UcTE strains in which the aas gene was inactivated and simultaneously an ability to express TE was provided.

(2) Inactivation of aas Gene, and Introduction of TE Gene and KAS Gene in Cyanobacteria The genomic DNA of the wild-type strains of *Synechococcus elongatus* sp. PCC7942 was used as a template, and the primer set of pUC118/NS1up-F (SEQ ID NO: 35) and NS1up/Kmr-R (SEQ ID NO: 36) described in Table 1 was used to amplify upstream fragments (NS1up fragments, SEQ ID NO: 20) of a neutral site NS1 region. Further, the genomic DNA was used as a template, and the primer set of Kmr/NS1down-F (SEQ ID NO: 37) and NS1down/pUC118-R (SEQ ID NO: 38) described in Table 1 was used to amplify downstream fragments (NS1down fragments, SEQ ID NO: 21) of the neutral site NS1 region. Furthermore, a pJH1 plasmid (Trieu-Cuot P et al., Gene, 1983, vol. 23, p. 331-341) was used as a template, and PCR was carried out by using the primers Kmr-F (SEQ ID NO: 39) and Kmr-R (SEQ ID NO: 40) described in Table 1 to amplify kanamycin resistance marker gene fragments (Km fragments: SEQ ID NO: 22).

The NS1up fragment, the NS1down fragment and the Km fragment as mentioned above were inserted into a place between the HincII sites of the pUC118 plasmid (manufactured by Takara Bio) by applying the In-Fusion (registered trademark) PCR Cloning method (Clontech) to obtain pUC118-NS1::Km plasmids.

The pUC118-NS1::Km plasmid was used as a template, and PCR was carried out by using the primers NS1up-R (SEQ ID NO: 41) and Kmr-F (SEQ ID NO: 39) described in Table 1 to linearize the pUC118-NS1::Km plasmid.

Further, PCR was carried out by using the primers 0918up/PrrnA-F (SEQ ID NO: 42) and PrrnA-R (SEQ ID NO: 43) described in Table 1 to perform PCR amplification of promoter region fragments (SEQ ID NO: 23) of an rrnA operon gene derived from Synechococcus elongatus sp. PCC7942.

Furthermore, a cDNA library of a KAS gene (NoKASIV gene, SEQ ID NO: 2) derived from Nannochloropsis oculata was prepared from Nannochloropsis oculata NIES-2145 strains. Then, the prepared cDNA library was used as a template, and PCR was carried out by using the primers PrrnA/NoKASIV-F (SEQ ID NO: 44) and NoKASIV/kmr-R (SEQ ID NO: 45) described in Table 1 to amplify NoKASIV gene fragments.

Then, the linearized pUC118-NS1::Km plasmid, the promoter region fragment of the rrnA operon gene and the NoKASIV gene fragment as mentioned above were mixed, and the resultant mixture was cloned by the In-Fusion (registered trademark) PCR Cloning method (Clontech) to obtain pUC118-NS1::PrrnA-NoKASIV-Km plasmids in which the promoter region fragment of the rrnA operon gene, the NoKASIV gene fragment and the Km fragment were inserted into the place between the neutral site NS1 regions in the genome of Synechococcus elongatus sp. PCC7942 in this order.

The Δ0918::UcTE strains were transformed by using the pUC118-NS1::PrrnA-NoKASIV-Km plasmid by the spontaneous transformation method, and the resultant material was selected by kanamycin resistance. Thus, ΔNS1::NoKASIVΔ0918::UcTE strains were obtained in which an ability to express KAS was provided by introducing a NoKASIV gene expression construct into a place between the NS1 regions on the genome, further the aas gene was inactivated and simultaneously the ability to express TE was provided by introducing the UcTE gene in which the codon was optimized into the place between the coding regions of the aas gene (Synpcc7942_0918 gene) on the genome.

(3) Production of Lipid Utilizing Transformant

In a 50 mL Erlenmeyer flask to which 25 mL of BG-11 medium having the composition shown in Table 2 below was added, the transformant was cultured for two weeks by setting an initial bacterial cell concentration to 0.2 in $OD_{730}$ by using a rotary shaker (120 rpm) at 30° C. under predetermined lighting (60 $\mu E \cdot m^{-2} \cdot sec^{-1}$). In addition, spectinomycin and/or kanamycin were added to the BG-11 medium to be 20 μg/mL in a concentration according to a kind of the transformant.

TABLE 2

Composition of BG-11 liquid medium

Stock solution

| | |
|---|---|
| A solution | 2 mL |
| B solution | 50 mL |
| C solution | 2 mL |
| D solution | 1 mL |

TABLE 2-continued

| | |
|---|---|
| E solution | 1 mL |
| 1.0M TES-KOH (pH 7.5) | 10 mL |
| Total | 1000 mL |

Composition of stock solution

| A solution | | B solution | |
|---|---|---|---|
| Citric acid•$H_2O$ | 0.33 g | $NaNO_3$ | 30 g |
| Ferric ammonium citrate | 0.3 g | $K_2HPO_4$ | 0.78 g |
| $Na_2EDTA$ | 0.05 g | $MgSO_4 \cdot 7H_2O$ | 1.5 g |
| total | 100 mL | total | 100 ml |

C solution $CaCl_2 \cdot 2H_2O$ 1.9 g/100 mL
D solution $Na_2CO_3$ 2 g/100 mL
E solution (the following substances are added)
[$H_3BO_3$ 2.86 g, $MnCl_2 \cdot 4H_2O$ 1.81 g, $ZnSO_4 \cdot 7H_2O$ 0.22 g, $CuSO_4 \cdot 5H_2O$ 0.08 g, $Na_2MoO_4$ 0.021 g, Co $(NO_3) \cdot 6H_2O$ 0.0494 g, conc•$H_2SO_4$ single drop, $H_2O$]/1000 mL After completion of the culture, 1 g of $NaH_2PO_4$ and 50 μL of 7-pentadecanone (1 mg/mL) dissolved as an internal standard in methanol were added to 25 mL of culture fluid. Then, 10 mL of hexane was added to this fluid, and the resultant mixture was sufficiently stirred and then left to stand for 10 minutes. The resultant mixture was centrifuged at 2,500 rpm for 10 minutes at room temperature, and then an upper layer portion was collected in an eggplant flask. Then, 5 mL of hexane was further added to a lower layer obtained by centrifugation, and the resultant mixture was stirred, centrifuged twice and concentrated in vacuum to obtain a dried sample.

0.7 mL of 0.5 N potassium hydroxide/methanol solution was added to the dried sample, and the resultant mixture was kept warm at 80° C. for 30 minutes. Then, 1 mL of 14% solution of boron trifluoride (manufactured by Sigma-Aldrich) was added to the sample, and the mixture was kept warm at 80° C. for 10 minutes. Thereafter, 1 mL of hexane and 1 mL of saturated saline were added thereto, and the mixture was vigorously stirred and then was left for 30 minutes at room temperature. Then, the hexane layer (upper layer) was collected to obtain fatty acid methyl esters.

The obtained fatty acid methyl esters were provided for gas chromatographic analysis. Using 7890A (Agilent Technologies), gas chromatographic analysis was performed under the conditions as follows.

(Analysis conditions)

Capillary column: DB-1 MS 30 m×200 μm×0.25 μm, (manufactured by J&W Scientific)

Mobile phase: high purity helium

P Flow rate inside the column: 1.0 mL/min

Temperature rise program: 100° C. (for 1 min.)→10° C./min→300° C. (for 5 min.)

Equilibration time: for 1 min.

Injection port: split injection (split ratio: 100:1), Pressure: 14.49 psi, 104 mL/min Amount of injection: 1 μL Cleaning vial: methanol/chloroform Detector temperature: 300° C.

Amounts of the fatty acid methyl esters were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples.

Then the amount of each of the fatty acids and the total amount thereof per liter of the culture fluid was calculated. Further, the amount of each of the fatty acids and a total amount of fatty acids in the Δ0918::UcTE strains were taken as 1 for each, and the amount of each of the fatty acids and the total amount of fatty acids in the ΔNS1::NoKASIVΔ0918::UcTE strains were calculated for each in terms of a relative value.

Table 3 shows the results. In addition, the results in Table 3 are shown in terms of an average value of the results of independent culture three times and chromatography analyses thereof.

TABLE 3

| | Fatty acid composition (Relative value of the results to that of Δ0918::UcTE) | | | | | (n = 3) |
|---|---|---|---|---|---|---|
| Genotype | Lauric acid (C12:0) | Myristic acid (C14:0) | Palmitic acid (C16:0) | Palmitoyl acid (C16:1) | Stearic acid, Oleic acid (C18:0, C18:1) | Total amount of fatty acids |
| Δ0918::UcTE | 1.00 | 1.00 | 1.00 | 1.00 | 1.00 | 1.00 |
| ΔNS1::KASIVΔ0918::UcTE | 1.53 | 1.62 | 0.77 | 0.59 | 1.19 | 1.43 |

As shown in Table 3, in the ΔNS1::NoKASIVΔ0918::UcTE strains, a total amount of production of fatty acids was increased by 1.43 times in comparison with the Δ0918::UcTE strains. Further, in the ΔNS1::NoKASIVΔ0918::UcTE strains, an amount of production of lauric acid and myristic acid, each being medium chain fatty acids, was also increased by 1.53 times to 1.62 times in comparison with the Δ0918::UcTE strains.

As described above, the transformant in which productivity of medium chain fatty acids and productivity of total fatty acids to be produced were improved can be prepared by introducing the KAS gene into cyanobacteria. Then, the productivity of medium chain fatty acids and a total amount of fatty acids to be produced can be improved by culturing this transformant.

Comparative Example Production of Lipid Utilizing KASIV Derived from *Cuphea lanceolata*

Lipid was produced in a manner similar to the Examples except that KAS derived from *Cuphea lanceolata* (hereinafter, referred to as "CIKASIV") was used in place of KAS derived from *Nannochloropsis oculata*.

Herein, an amino acid sequence of CIKASIV is set forth in SEQ ID NO: 48. Then, a nucleotide sequence of a gene encoding CIKASIV (hereinafter, referred to as "CIKASIV gene") is set forth in SEQ ID NO: 49. In addition, identity of the amino acid sequence of CIKASIV to the amino acid sequence set forth in SEQ ID NO: 1 is 38.5%. Moreover, identity of the nucleotide sequence of the CIKASIV gene to the nucleotide sequence set forth in SEQ ID NO: 2 is 49%.

(1) Preparation of Plasmid for CIKASIV Gene Expression

The above-mentioned pUC118-NS1::Km plasmid was used as a template, and PCR was carried out by using the primers NS1up-R (SEQ ID NO: 41) and Kmr-F (SEQ ID NO: 39) described in Table 1 to linearize the pUC118-NS1::Km plasmid.

Moreover, PCR was carried out by using the primers 0918up/PrrnA-F (SEQ ID NO: 42) and PrrnA-R (SEQ ID NO: 43) described in Table 1 to perform PCR amplification of promoter region fragments (SEQ ID NO: 23) of an rrnA operon gene derived from *Synechococcus elongatus* sp. PCC7942.

A gene sequence encoding CIKASIV (SEQ ID NO: 49; Accession number: AJ344250.1; Shutt B S et al., "Beta-ketoacyl-acyl carrier protein synthase IV: a key enzyme for regulation of medium-chain fatty acid synthesis in *Cuphea lanceolata* seeds" Planta. 2002 September; 215(5), p. 847-854) was artificially synthesized. The synthesized DNA fragment was used as a template, and PCR was carried out by using the primer PrrnA/CIKASIV-F (SEQ ID NO: 50) and the primer CIKASIV/Kmr-R (SEQ ID NO: 51) described in Table 1 to amplify CIKASIV gene fragments.

Then, the linearized pUC118-NS1::Km plasmid, the promoter region fragment of the rrnA operon gene and the CIKASIV gene fragment as described above were mixed, and the resultant mixture was cloned by the In-Fusion (registered trademark) PCR Cloning method (Clontech) to obtain a pUC118-NS1::PrrnA-CIKASIV-Km plasmid in which the promoter region fragment of the rrnA operon gene, the CIKASIV gene fragment and the Km fragment were inserted into a place between neutral site NS1 regions in a genome of *Synechococcus elongatus* sp. PCC7942 in this order.

(2) Preparation of Transformant and Production of Lipid

A transformant (ΔNS1::CIKASIVΔ0918::UcTE) was prepared in a manner similar to the Examples except that the pUC118-NS1::PrrnA-CIKASIV-Km plasmid was used in place of the pUC118-NS1::PrrnA-NoKASIV-Km plasmid.

Then, lipid was produced by using the prepared transformant in a manner similar to the Examples and fatty acids were analyzed. Table 4 shows the results.

TABLE 4

| | Fatty acid composition (Relative value of the results to that of Δ0918::UcTE) | | | | | |
|---|---|---|---|---|---|---|
| Genotype | Lauric acid (C12:0) | Myristic acid (C14:0) | Palmitic acid (C16:0) | Palmitoyl acid (C16:1) | Stearic acid, Oleic acid (C18:0, C18:1) | Total amount of fatty acids |
| Δ0918::UcTE | 1.00 | 1.00 | 1.00 | 1.00 | 1.00 | 1.00 |
| ΔNS1::CIKASIVΔ0918::UcTE | 0.92 | 0.80 | 0.53 | 0.88 | 1.35 | 0.87 |

As shown in Table 5, with regard to ΔNS1::CIKASIVΔ0918::UcTE strains, both a total amount of production of fatty acids and an amount of production of medium chain fatty acids (lauric acid and myristic acid) were decreased in comparison with Δ0918::UcTE strains.

As described above, even if a KAS gene derived from *Cuphea lanceolate* is introduced into cyanobacteria, a desired effect of the present invention is unable to be obtained.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-104991 filed in Japan on May 22, 2015, which is entirely herein incorporated by reference.

The invention claimed is:

1. A method of producing fatty acids or a lipid containing the fatty acids as components, comprising the steps of:
   culturing a cyanobacterium that has been transformed with a polynucleotide comprising a nucleotide sequence encoding the following protein (a) or (b), and producing fatty acids or a lipid containing the fatty acids as components:
   (a) a protein consisting of the amino acid sequence set forth in SEQ ID NO: 1; and
   (b) a protein having β-ketoacyl-ACP synthase activity and consisting of an amino acid sequence having 95% or more sequence identity with the amino acid sequence of SEQ ID NO: 1.

2. The method of claim 1, wherein the lipid is a medium chain fatty acid or an ester thereof.

3. The method of claim 1, wherein the protein (a) or (b) is a β-ketoacyl-ACP synthase that has substrate specificity for a medium chain acyl-ACP.

4. The method of claim 1, wherein the cyanobacterium is further transformed with a polynucleotide encoding an acyl-ACP thioesterase that has substrate specificity for a medium chain acyl-ACP.

5. The method of to claim 4, wherein the acyl-ACP thioesterase is at least one acyl-ACP thioesterase selected from the group consisting of
   acyl-ACP thioesterase of *Cocos nucifera*,
   acyl-ACP thioesterase of *Cinnamonum camphorum*,
   acyl-ACP thioesterase of *Nannochloropsis oculata*,
   acyl-ACP thioesterase of *Umbellularia californica*,
   acyl-ACP thioesterase of *Nannochloropsis gaditana*,
   acyl-ACP thioesterase of *Nannochloropsis granulata*, and
   acyl-ACP thioesterase of *Symbiodinium microadriaticum*.

6. The method of claim 1, wherein the cyanobacterium is a member of the genus *Synechocystis* or the genus *Synechococcus*.

7. The method of claim 1, wherein a gene encoding an acyl-ACP synthetase in the cyanobacterium is deleted or inactivated.

8. The method of claim 7, wherein the acyl-ACP synthetase gene that is deleted or inactivated in the cyanobacterium is selected from the group consisting of
   an acyl-ACP synthetase gene of *Synechocystis* sp. PCC6803,
   an acyl-ACP synthetase gene of *Synechocystis* sp. PCC7509,
   an acyl-ACP synthetase gene of *Synechococcus elongatus* sp. PCC7942,
   an acyl-ACP synthetase gene of *Thermosynechococcus elongatus* BP-1,
   an acyl-ACP synthetase gene of *Trichodesmium erythraeum* IMS101,
   an acyl-ACP synthetase gene of *Acaryochloris mariana* MBIC11017,
   an acyl-ACP synthetase gene of *Crocosnhaera watsonii* WH8501, and
   an acyl-ACP synthetase gene of *Anabaena* sp. PCC7120.

9. The method of claim 1, wherein the productivity of lauric acid and myristic acid is enhanced as compared to that of a cyanobacterium that is the same as the transformed cyanobacterium except that it has not been transformed with the polynucleotide.

10. A method of enhancing lipid productivity in a cyanobacterium, comprising transforming the cyanobacterium with a polynucleotide comprising a nucleotide sequence encoding the following protein (a) or (b), thereby enhancing productivity of the lipid in the transformed cyanobacterium:
    (a) a protein consisting of the amino acid sequence set forth in SEQ ID NO: 1; and
    (b) a protein having β-ketoacyl-ACP synthase activity and consisting of an amino acid sequence having 95% or more sequence identity with the amino acid sequence of SEQ ID NO: 1.

11. The method of claim 10, wherein the lipid is a medium chain fatty acid or an ester thereof.

12. The method of claim 10, wherein the protein (a) or (b) is a β-ketoacyl-ACP synthase that has substrate specificity for a medium chain acyl-ACP.

13. The method of claim 10, wherein the cyanobacterium is further transformed with a polynucleotide encoding an acyl-ACP thioesterase that has substrate specificity for a medium chain acyl-ACP.

14. The method of claim 13, wherein the acyl-ACP thioesterase is at least one acyl-ACP thioesterase selected from the group consisting of
    acyl-ACP thioesterase of *Cocos nucifera*,
    acyl-ACP thioesterase of *Cinnamonum camphorum*,
    acyl-ACP thioesterase of *Nannochloropsis oculata*,
    acyl-ACP thioesterase of *Umbellularia californica*,
    acyl-ACP thioesterase of *Nannochloropsis gaditana*,
    acyl-ACP thioesterase of *Nannochloropsis granulata*, and
    acyl-ACP thioesterase of *Symbiodinium microadriaticum*.

15. The method of claim 10, wherein the cyanobacterium is a member of the genus *Synechocystis* or the genus *Synechococcus*.

16. The method of claim 10, wherein a gene encoding an acyl-ACP synthetase in the cyanobacterium is deleted or inactivated.

17. The method of claim 16, wherein the acyl-ACP synthetase gene that is deleted or inactivated in the cyanobacterium is selected from the group consisting of
    an acyl-ACP synthetase gene of *Synechocystis* sp. PCC6803,
    an acyl-ACP synthetase gene of *Synechocystis* sp. PCC7509,
    an acyl-ACP synthetase gene of *Synechococcus elongatus* sp. PCC7942,
    an acyl-ACP synthetase gene of *Thermosynechococcus elongatus* BP-1,
    an acyl-ACP synthetase gene of *Trichodesmium erythraeum* IMS101,
    an acyl-ACP synthetase gene of *Acaryochloris mariana* MBIC11017, an acyl-ACP synthetase gene of *Crocosnhaera watsonii* WH8501, and an acyl-ACP synthetase gene of *Anabaena* sp. PCC7120.

18. The method of claim 10, wherein the lipid produced by the transformant is secreted outside cells of the transformant.

19. The method of claim 10, wherein the productivity of lauric acid and myristic acid is enhanced as compared to that of a cyanobacterium that is the same as the transformed cyanobacterium except that it has not been transformed with the polynucleotide.

* * * * *